(12) United States Patent
Hopenfeld

(10) Patent No.: US 9,220,428 B2
(45) Date of Patent: *Dec. 29, 2015

(54) HEART RATE CORRECTION SYSTEM AND METHODS FOR THE DETECTION OF CARDIAC EVENTS

(71) Applicant: ANGEL MEDICAL SYSTEMS, INC., Fair Haven, NJ (US)

(72) Inventor: Bruce Hopenfeld, Salt Lake City, UT (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/681,472

(22) Filed: Apr. 8, 2015

(65) Prior Publication Data

US 2015/0208941 A1 Jul. 30, 2015

Related U.S. Application Data

(62) Division of application No. 12/461,442, filed on Aug. 12, 2009, now Pat. No. 9,042,969.

(51) Int. Cl.
*A61B 5/04* (2006.01)
*A61B 5/0452* (2006.01)
(Continued)

(52) U.S. Cl.
CPC ............ *A61B 5/04012* (2013.01); *A61B 5/0245* (2013.01); *A61B 5/0402* (2013.01); *A61B 5/0452* (2013.01)

(58) Field of Classification Search
CPC ....... A61B 5/0452; A61B 5/04; A61B 5/0402
USPC .......................................... 600/508, 509, 515
See application file for complete search history.

(56) References Cited

U.S. PATENT DOCUMENTS 4,832,038 A 5/1989 Arai et al.
5,596,993 A 1/1997 Oriol et al.
(Continued)

OTHER PUBLICATIONS

Bosnjak et al., "An approach to intelligent ischaemia monitoring", Medical & Biological Engineering & Computing (Nov. 1995) 33(6):749-756.

(Continued)

*Primary Examiner* — Catherine Voorhees
*Assistant Examiner* — Roland Dinga
(74) *Attorney, Agent, or Firm* — Rosenberg, Klein & Lee

(57) ABSTRACT

A device for detecting a cardiac event is disclosed. Detection of an event is based on a test applied to a parameter whose value varies according to heart rate. Both the parameter value and heart rate (RR interval) are filtered with an exponential average filter. From these filtered values, the average change in the parameter and the RR interval are also computed with an exponential average filter. Before computing the average change in the parameter, large changes in the parameter over short times, which may be caused by body position shifts, are attenuated are removed, so that the average change represents an average of small/smooth changes in the parameter's value that are characteristic of acute ischemia, one of the cardiac events that may be detected. The test to detect the cardiac event depends on the heart rate, the difference between the parameter's value and its upper and lower normal values, and its average change over time, adjusted for heart rate changes. The upper and lower normal parameter values as a function of heart rate are determined from long term stored data of the filtered RR values and parameter values. Hysteresis related data and transitory deviations from normal (e.g. vasospasm related data) are excluded from the computation of normal upper and lower parameter bounds.

9 Claims, 16 Drawing Sheets

(51) Int. Cl.
  *A61B 5/0245* (2006.01)
  *A61B 5/0402* (2006.01)

(56) References Cited

U.S. PATENT DOCUMENTS

| | | |
|---|---|---|
| 6,272,379 B1 | 8/2001 | Fischell et al. |
| 6,339,720 B1 | 1/2002 | Anzellini et al. |
| 6,397,100 B2 | 5/2002 | Stadler et al. |
| 6,609,023 B1 | 8/2003 | Fischell et al. |
| 7,001,337 B2 | 2/2006 | Dekker |
| 7,283,865 B2 | 10/2007 | Noran |
| 7,512,438 B2 | 3/2009 | Fischell et al. |
| 7,558,623 B2 | 7/2009 | Fischell et al. |
| 8,630,702 B2 | 1/2014 | Fischell et al. |
| 8,838,215 B2 | 9/2014 | John et al. |
| 2004/0215092 A1 * | 10/2004 | Fischell et al. ............. 600/515 |
| 2009/0076403 A1 | 3/2009 | Hopenfeld |
| 2009/0105601 A1 | 4/2009 | Kamata |

OTHER PUBLICATIONS

Kligfield et al., "Heart Rate Adjustment of ST Segment Depression for Improved Detection of Coronary Artery Disease", Circulation (1989) 79(2):245-255.

Kligfield & Lauer, "Exercise Electrocardiogram Testing: Beyond the ST Segment", Circulation (2006) 114 (19):2070-2082.

Smrdel & Jager, "Automated detection of transient ST-segment episodes in 24 h electrocardiograms", Medical Biological Engineering & Computing (May 2004) 42(3):303-311.

* cited by examiner

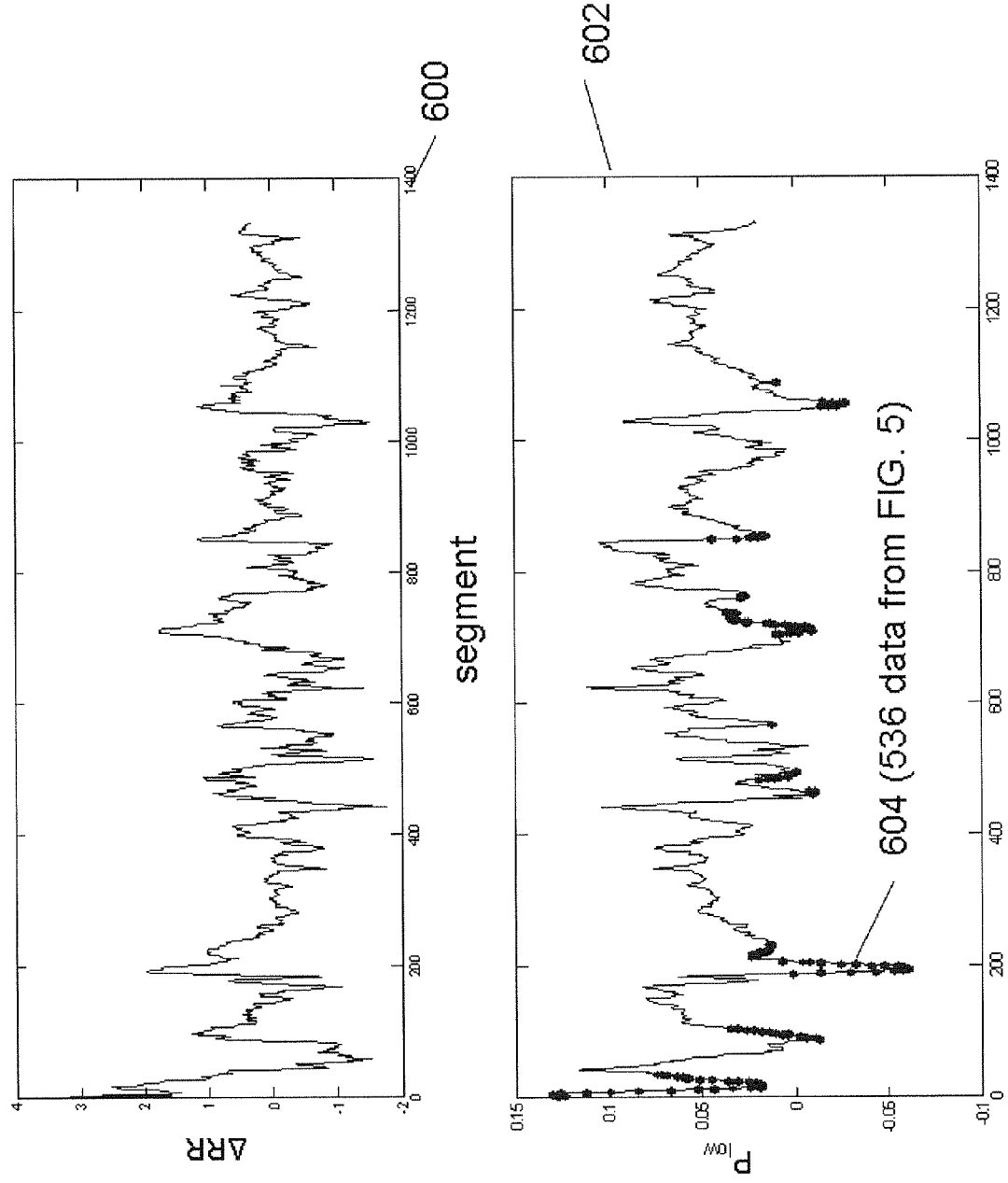

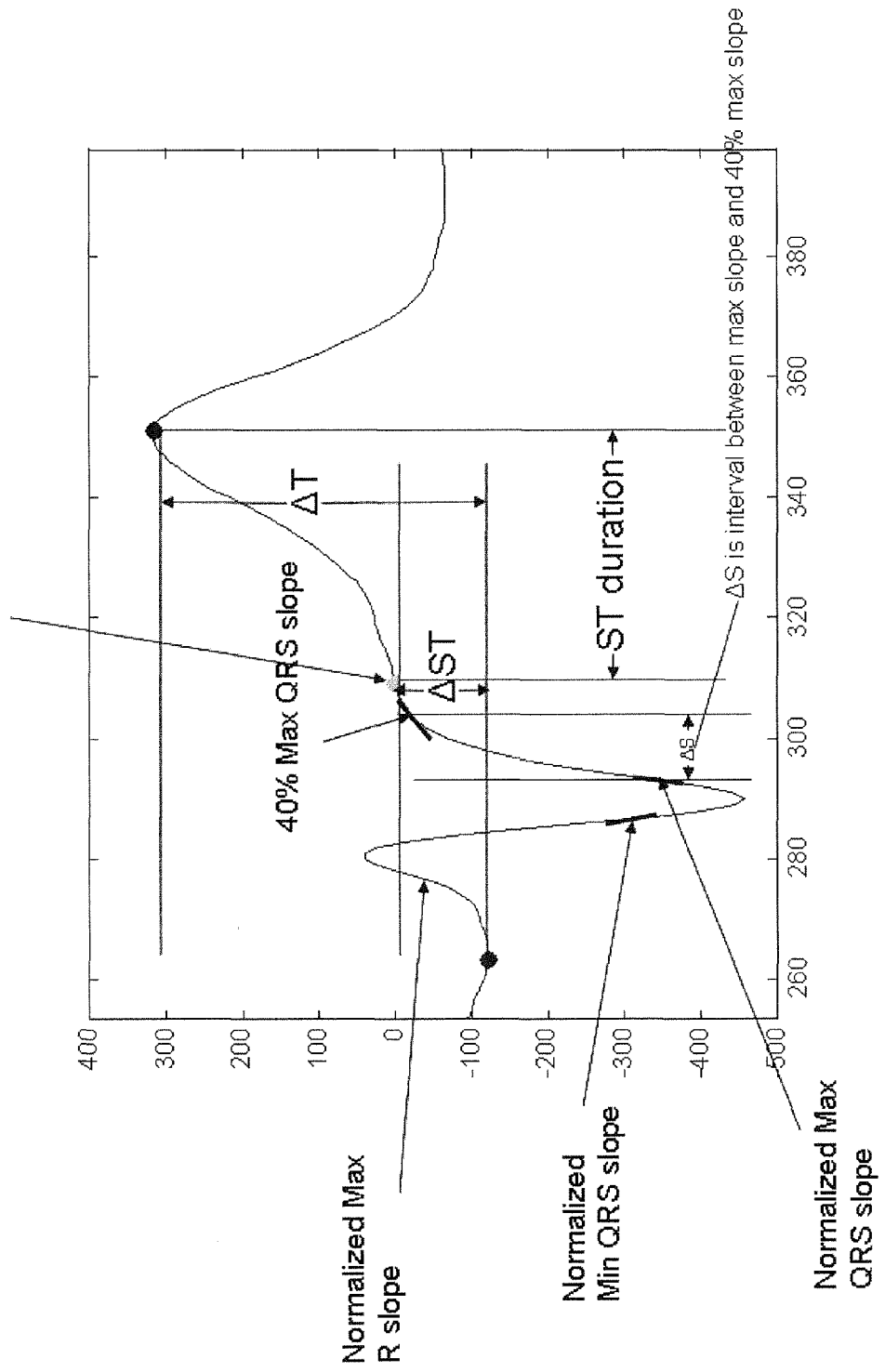

FIG. 12a

| Condition | Cause | Parameter | Time Frame |
|---|---|---|---|
| atrial fibrillation | | RR interval; lack of p-wave | immediate |
| Congestive heart failure decompensation | Heart-electrical and pressure; edema | ST/T/U (Global); QRS changes | Hours/days |
| Chronic ischemia | | ST/T/U (Global + Local); QRS changes | days-months |
| Other arrhythmia | | RR interval; $T_{amp}/ST_{dur}$ vs. heart rate | |
| Anemia | global ischemia; possibly local | ST/T/U (Global); QRS changes | hours |
| Electrolyte imbalances | | ST/T/U (Global) | hours |

FIG. 12b

| | | |
|---|---|---|
| hypertrophy | QRS changes | |
| Apical ballooning | ST/T/U | |
| Sugar imbalances | ST/T/U (Global) | |
| Bundle branch block | ST/T/U; QRS changes | |
| drugs | ST/T/U (Global) | |
| Pericarditis/myocarditis/ Chagas disease | ST/T/U (Global) | Hours/days |
| Neurogenic - stroke/hemorrhage/trauma etc. | ST/T/U (Global) | Minutes/hours |

HEART RATE CORRECTION SYSTEM AND METHODS FOR THE DETECTION OF CARDIAC EVENTS

REFERENCE TO RELATED APPLICATION

This Application is being filed as a Divisional Patent Application based on application Ser. No. 12/461,442, filed 12 Aug. 2009, currently pending.

FIELD OF USE

This invention is in the field of medical device systems that monitor a patient's cardiovascular condition.

BACKGROUND OF THE INVENTION

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

There are a number of portable monitors that attempt to detect AMI. Monitors that include wearable sensors (e.g. a medical-vest with electrodes) may be somewhat inconvenient for patients. Chronically implanted sensors provide the possibility for continuous monitoring without many of the inconveniences associated with wearable monitors. One type of implantable monitor known as the Guardian (Angel Medical Systems, the assignee of the present invention), which is currently undergoing clinical trials in the United States, includes an electrode chronically implanted within the heart. An intracardiac electrode may provide a strong signal at the cost of requiring intracardiac implantation. Another type of implantable monitor can rely upon subcutaneous electrodes, which are less invasive, but receive smaller amplitude signals compared to intracardiac electrodes.

Regardless of the device, many parameters that are involved in heart monitoring are heart rate dependent. Handling heart rate dependence of parameters presents a difficult problem.

U.S. patent application Ser. No. 11/594,806, invented by Fischell et al., filed November, 2006, entitled "System for the Detection of Different Types of Cardiac Events" describes an implantable cardiac event monitor that detects acute ischemia based on ST segment shifts. The described device categorizes electrogram segments according to heart rate; different heart rate ranges (e.g. 60 beats/min.-90 beats/min. and 91 beats/min.-110 beats/min.) are associated with different thresholds for detecting ischemia. The '806 application also describes requiring ST segment changes to persist before acute ischemia is detected; the persistence criteria may be heart rate dependent. U.S. Pat. No. 6,609,023 to Fischell et al., issued August 2003, also describes persistence criteria.

U.S. patent application Ser. No. 11/898,673, invented by Hopenfeld and owned by the assignee of the present invention, filed September 2007, entitled "Waveform Feature Value Averaging System and Methods for the Detection of Cardiac Events", describes cardiac event detection tests that involve computing the average change in a parameter over time. (E.g. Average ST segment change of 3%/minute.)

In the context of body surface electrocardiograms, it is known that ST changes persist after recovery from exercise (i.e. high heart rate). Indeed, the trajectory of the ST vs. heart rate curve after exercise has been proposed as a marker for coronary artery disease. (Kligfield P, Lauer M S. "Exercise electrocardiogram testing: beyond the ST segment." *Circulation.* 2006 Nov. 7; 114(19):2070-82.) The slope of the ST/HR curve in the setting of exercise stress testing has also been proposed as a marker for ischemia. Id. It also known to use of the slope of the ST/HR curve as a marker for chronic ischemia. Kligfield P, Ameisen O, Okin P M. Heart rate adjustment of ST-segment depression for improved detection of coronary artery disease. *Circulation.* 1989; 79(2):245-55.

Dealing with heart rate changes poses difficulties. One possibility for handling this problem is described in U.S. patent application Ser. No. 11/710,902 to John et al., filed Feb. 27, 2007, entitled "Systems and methods of medical monitoring according to patient state. According to this application, parameter thresholds are adjusted after a heart rate change has occurred. An alternative is described in the '806 application, which involves detecting whether a heart rate has changed, and excluding data associated with heart rate changes from cardiac detection tests.

In U.S. Pat. No. 6,397,100 to Stadler and Shannon, ST segment values are low pass filtered to ensure that very rapid changes, which may be caused by axis shifts, are not considered to be ST shifts caused by ischemia. Two different low pass filters are applied, resulting in two different filtered signals. One filtered signal is representative of very slow ST band drift. The other filtered signal is representative of the true ST level excluding high frequency axis shift. ST segment deviation indicative of ischemia is equal to the difference between the filtered signals.

Despite all of the foregoing work that has been done, there is still a need for an effective subcutaneous or surface based system for monitoring ischemia.

SUMMARY OF THE INVENTION

An embodiment of the present invention comprises a system that includes an implanted cardiac detection and/or diagnostic device and external equipment. The battery powered implantable cardiac diagnostic device contains electronic circuitry that can detect a cardiac event such as an acute myocardial infarction and warn the patient when the event, or a clinically relevant precursor, occurs. The cardiac diagnostic device can store the patient's electrogram for later readout and can send wireless signals to and receive wireless signals from the external equipment.

The cardiac diagnostic device receives electrical signals from subcutaneous or body surface sensors. One pair of electrodes comprises a lead sensor that senses the potential between the upper right clavicle and a medial region over the area of the sternum. Such a lead is oriented substantially along the long axis of the heart and is therefore capable of detecting current flow between the epicardium and endocardium, which at least in part dictates T wave timing.

The cardiac diagnostic device includes a processor that computes QRS onset and offset points and fiducial points associated with T waves.

The processor then computes averages of various waveform feature values, including a QRS measure sensitive to QRS curvature, T wave timing measures, ST segment deviation (difference between signal amplitudes at QRS offset and onset and/or minimum amplitude between QRS offset and peak T wave); and T/U wave amplitudes. These averages are preferably computed by exponential averaging. From the exponential averages parameter, the processor computes a filtered average of the change in the averages over time that eliminates large changes (e.g. that may be caused by axis shifts). The RR interval is also preferably computed with exponential averaging and the average change in RR interval over time (e.g. average decrease of X beats/minute/minute). Based on the averaged parameter values and their associated averaged RR intervals, which indicate the appropriate heart related thresholds to apply, and the change in the averages (e.g. average change of 3%/minute), the processor applies a test to determine the likelihood that a cardiac event has occurred. The specifics are further described below. A different test, or no test at all, is applied to parameter values associated with large changes in heart rate.

Averaged/filtered parameter value data is collected over a range of averaged/filtered RR intervals. The normal upper and lower bounds of this data define upper and lower bound curves that are a function of heart rate. By computing and examining an average change in the heart rate over a short time interval, effects parameter values associated with hysteresis can be removed from the normal ranges and also removed from cardiac event detection. Alternatively, the ischemia test may takine the average change in the heart into account by, e.g., expanding detection thresholds to account for larger parameter dispersion and/or by adjusting the normal boundary to account for the hysteresis.

Transitory events such as vasospasms are also detected. The associated parameter values are preferably excluded from the range of normal parameter values.

Parameter values at any RR interval (P(RR)) are compared with both higher and lower band curves $B_{high}(RR)$ and $B_{low}(RR)$. This results in two trajectories: a positive trajectory (i.e. $P(RR)-B_{high}(RR); P(RR)-B_{high}(RR)$.) The cardiac event test involves comparing the value of these trajectories at a particular time with a threshold e.g. $P(RR)_{,i}-B_{high}(RR)_{,i}$ ($=P_{high}$)<threshold, where the subscript "i" denotes time/segment i. To detect a cardiac event, $P_{high}$ (or $P_{low}=P(RR)_{,i}-B_{low}(RR)_{,i}$) must remain below threshold for a period of time. The cardiac event detection test also involves comparing filtered, averaged changes in $P_{high}$ ($\Delta P_{high}$) and $P_{low}$ ($\Delta P_{low}$) (e.g. x % change/minute) are also compared with thresholds. The event may be detected as a sliding scale function that weights both the absolute parameter deviation ($P_{high}$ or $P_{low}$) and the averaged/filtered change in $P_{high}$ or $P_{low}$ over time.

Taking into account the timing of the change in ($P_{high}$ or $P_{low}$) can increase specificity of the cardiac event detection test by eliminating high frequency noise (e.g. axis shift changes) and matching a pathology with its expected time course of change. E.g. acute ischemia generally produces changes over a few minutes whereas pericarditis might produce changes over many hours.

The cardiac event test preferably involves a number of parameters, including: ST deviation, ST interval duration (time between QRS offset and peak T wave), QRS duration, and QRS slope/curvature parameters. Both the absolute value and the change in these parameters are compared to thresholds, as described above. If any test for any parameter is positive, then the cardiac event test as a whole is considered positive. For example, assume that a (heart rate corrected) normal upper bound QRS duration is 115 ms. If the QRS duration is 125 ms for a number of segments, then the cardiac event test is positive. Alternatively, if the QRS duration is 120 ms and the average/filtered increase in QRS duration is 3 ms/minute for the past three minutes, which exceeds a QRS change threshold of 2 ms/minute, the cardiac event is again detected.

Continuing with the above example, if there are no QRS duration changes but there is a significant decrease in ST duration, the cardiac event may again be detected. Assuming a (heart rate corrected) normal lower bound ST duration of 250 ms, if the ST duration is 220 ms for a number of segments, then the cardiac event test is positive. Alternatively, if the ST duration is 240 ms and the average/filtered decrease in ST duration is 10 ms/minute for the past three minutes, which exceeds an ST duration change threshold of 5 ms/minute, the cardiac event is again detected.

Still continuing with the above example, it may be desirable in some cases to combine different parameters in an "and" fashion. If the average QRS duration increase is 1 ms/minute (less than the above mentioned threshold for detection of 2 ms/minute) over three minutes, and the average ST duration decrease over the same period is 3 ms/minute (less than the above mentioned threshold for detection of 5 ms/minute), the cardiac event may nonetheless be detected due to the combined changes in QRS duration and ST duration.

BRIEF DESCRIPTION OF THE DRAWINGS

FIG. 6 shows a plot of a parameter trajectory along with the associated average change in heart rate.

FIG. 11 is an example of some of the parameters that may be processed by the method outlined with respect to FIGS. 7 and 8.

FIGS. 12a and 12b are a table of are a table that shows various pathologies and associated electrocardiographic changes, including the likely time course of such changes.

DETAILED DESCRIPTION OF THE INVENTION

Architecture

Figure 1:
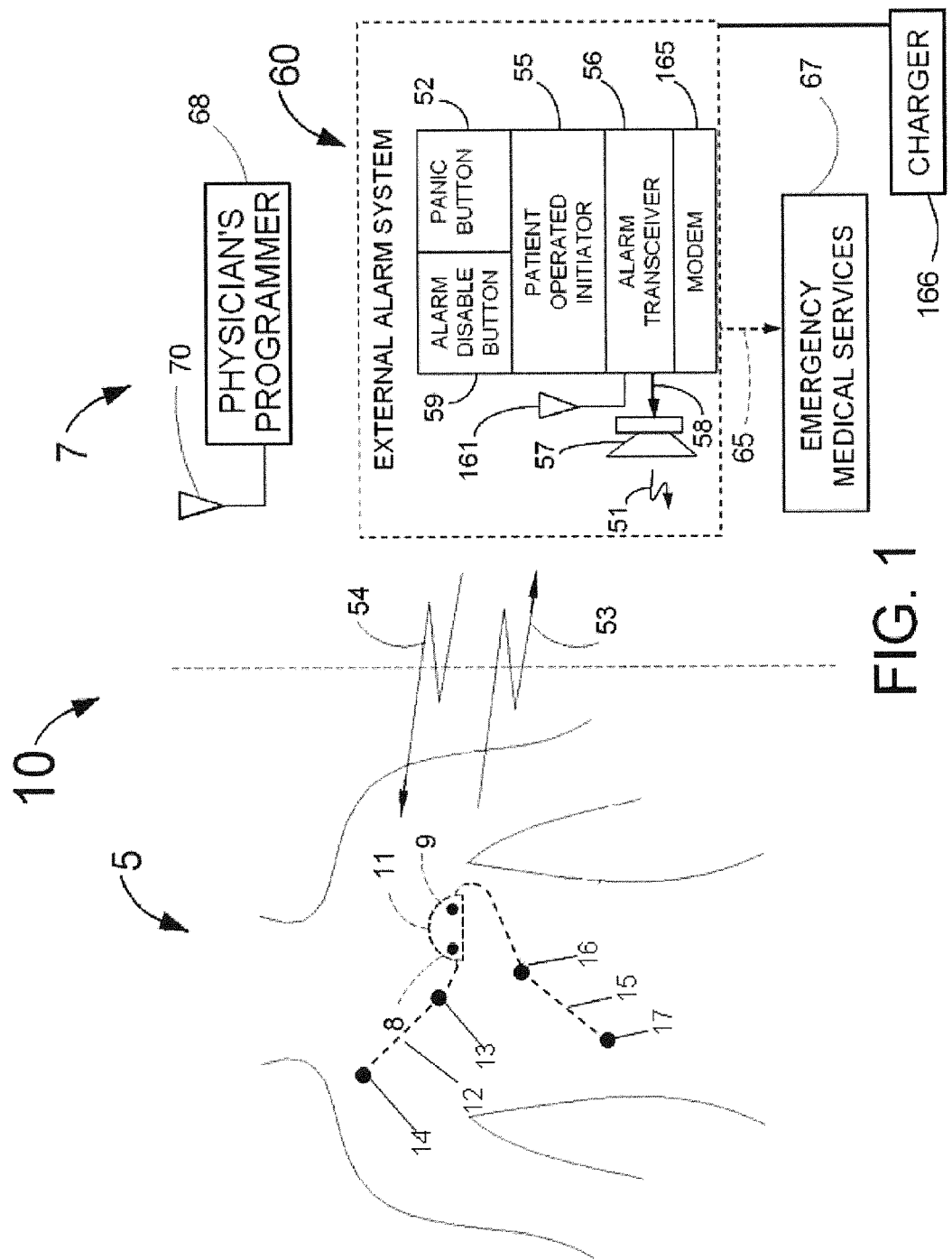
FIG. 1 illustrates a system for the detection of a cardiac event and for warning the patient that a medically relevant cardiac event is occurring.

FIG. 1 illustrates one embodiment of a system 10 comprising an implanted cardiac diagnostic device 5 and external equipment 7. The battery powered cardiac diagnostic device 5 contains electronic circuitry that can detect a cardiac event such as an acute myocardial infarction or arrhythmia and warn the patient when the event, or a clinically relevant precursor, occurs. The cardiac diagnostic device 5 can store the patient's electrogram for later readout and can send wireless signals 53 to and receive wireless signals 54 from the external equipment 7. The functioning of the cardiac diagnostic device 5 will be explained in greater detail with the assistance of FIG. 2.

The cardiac diagnostic device 5 receives electrical signals from subcutaneous or body surface leads 12 and 15. Clavicle lead 12 comprises electrodes 13 and 14 with polarity hereafter defined as the difference potential measured between electrode 13 and electrode 14. Right side lead 15 comprises electrodes 16 and 17 with polarity hereafter defined as the potential at electrode 16 minus the potential at electrode 17. The clavicle side lead 12 measures the electrical signal between the upper right clavicle and a medial region over the area of the sternum and is therefore generally less than 15 cm long; the right side lead is approximately aligned with the long axis of the heart. The right side lead 15 measures the electrical signal between the right precordial chest region and an inferior right lateral or posterior torso position. The cardiac diagnostic device 5 is housed in a metal case 11 that can serve as another electrode. The cardiac device 5 is shown in the left upper pectoral region but may be implanted in any convenient location such as the upper right pectoral region.

FIG. 1 also shows the external equipment 7 that consists of a physician's programmer 68 having an antenna 70, an external alarm system 60 including a charger 166. The external equipment 7 provides means to interact with the cardiac diagnostic device 5. These interactions include programming the cardiac diagnostic device 5, retrieving data collected by the cardiac diagnostic device 5 and handling alarms generated by the cardiac diagnostic device 5. The operation of these components is further described in U.S. patent application publication number 2004/0215092.

Figure 2:
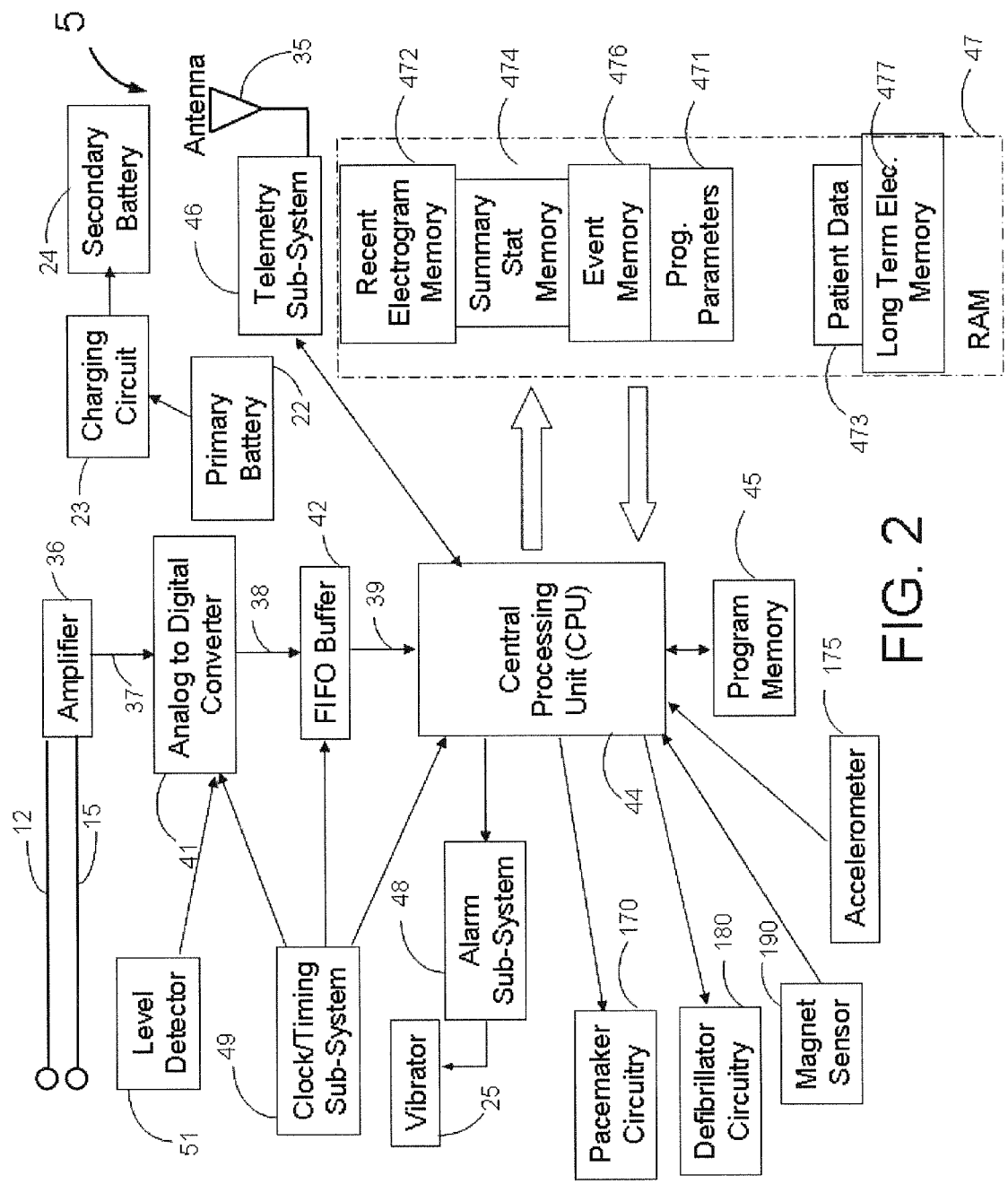
FIG. 2 is a block diagram of an implanted cardiac diagnostic system according to the present invention.

FIG. 2 is a block diagram of the cardiac diagnostic device 5 with primary battery 22 and a secondary battery 24. The secondary battery 24 is typically a rechargeable battery of smaller capacity but higher current or voltage output than the primary battery 22 and is used for short term high output components of the cardiac diagnostic device 5 like the RF chipset in the telemetry sub-system 46 or the vibrator 25 attached to the alarm sub-system 48. According to a dual battery configuration, the primary battery 22 will charge the secondary battery 24 through the charging circuit 23. The primary battery 22 is typically a larger capacity battery than the secondary battery 24. The primary battery also typically has a lower self discharge rate as a percentage of its capacity than the secondary battery 24. It is also envisioned that the secondary battery could be charged from an external induction coil by the patient or by the doctor during a periodic check-up.

The pairs of wires corresponding to leads 12 and 15 respectively connect to the amplifier 36, which is a multi-channel or differential amplifier. The amplified electrogram signals 37 from the amplifier 36 are then converted to digital signals 38 by the analog-to-digital converter 41, which preferably samples at a rate of 200 Hz. The temporal resolution of the sampling is relevant with regard to the sampling of the high frequency components of a heartbeat's activation (QRS) complex. The digital electrogram signals 38 are buffered in the First-In-First-Out (FIFO) memory 42. Processor means shown in FIG. 2 as the central processing unit (CPU) 44 coupled to memory means shown in FIG. 2 as the Random Access Memory (RAM) 47 can process the digital electrogram data 38 stored the FIFO 42 according to the programming instructions stored in the program memory 45. This programming (i.e. software) enables the cardiac diagnostic device 5 to detect the occurrence of a cardiac event such as an acute myocardial infarction.

A level detector 51 is coupled to the analog to digital converter 41. The level detector 51 detects whether a patient's torso is upright or supine and also, if the torso is supine, the extent of its rotation with respect to the earth (e.g. patient is lying flat on his/her back, lying on his/her right side or left side.) Many MEMS based level detects which can also operationally serve as inclinometers, accelerometers, and general detectors for motion/force exist.

Additional sensors may communicate with the device 5 wirelessly through the telemetry sub-system. The data from these leads may correspond to digitized electrogram signals (that have been processed by a remote subcutaneous device).

The operation of most of the components in FIG. 2 is further described in U.S. patent application publication number 2004/0215092.

In a preferred embodiment of the present invention the RAM 47 includes specific memory locations for 4 sets of electrogram segment storage. These are the recent electrogram storage 472 that would store the last 2 to 10 minutes of recently recorded electrogram segments so that the electrogram data occurring just before the onset of a cardiac event can be reviewed at a later time by the patient's physician using the physician's programmer 68 of FIG. 1. For example, the recent electrogram storage 472 might contain eight 10-second long electrogram segments that were captured every 30 seconds over the last 4 minutes.

A summary statistics memory 474 would provide storage for summary information, such as running averages, of various cardiac waveform feature values. A long term electrogram memory 477 would provide storage for electrograms collected over a relatively long period of time. In the preferred embodiment, every ninth electrogram segment that is acquired is stored in a circular buffer, so that the oldest electrogram segments are overwritten by the newest one.

The telemetry sub-system 46 with antenna 35 provides the cardiac diagnostic device 5 the means for two-way wireless communication to and from the external equipment 7 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the cardiac diagnostic device 5. It is also envisioned that standard wireless protocols such as Bluetooth and 802.11a or 802.11b might be used to allow communication with a wider group of peripheral devices.

Heart Rate Dependent Parameter Dynamics

Figure 3:
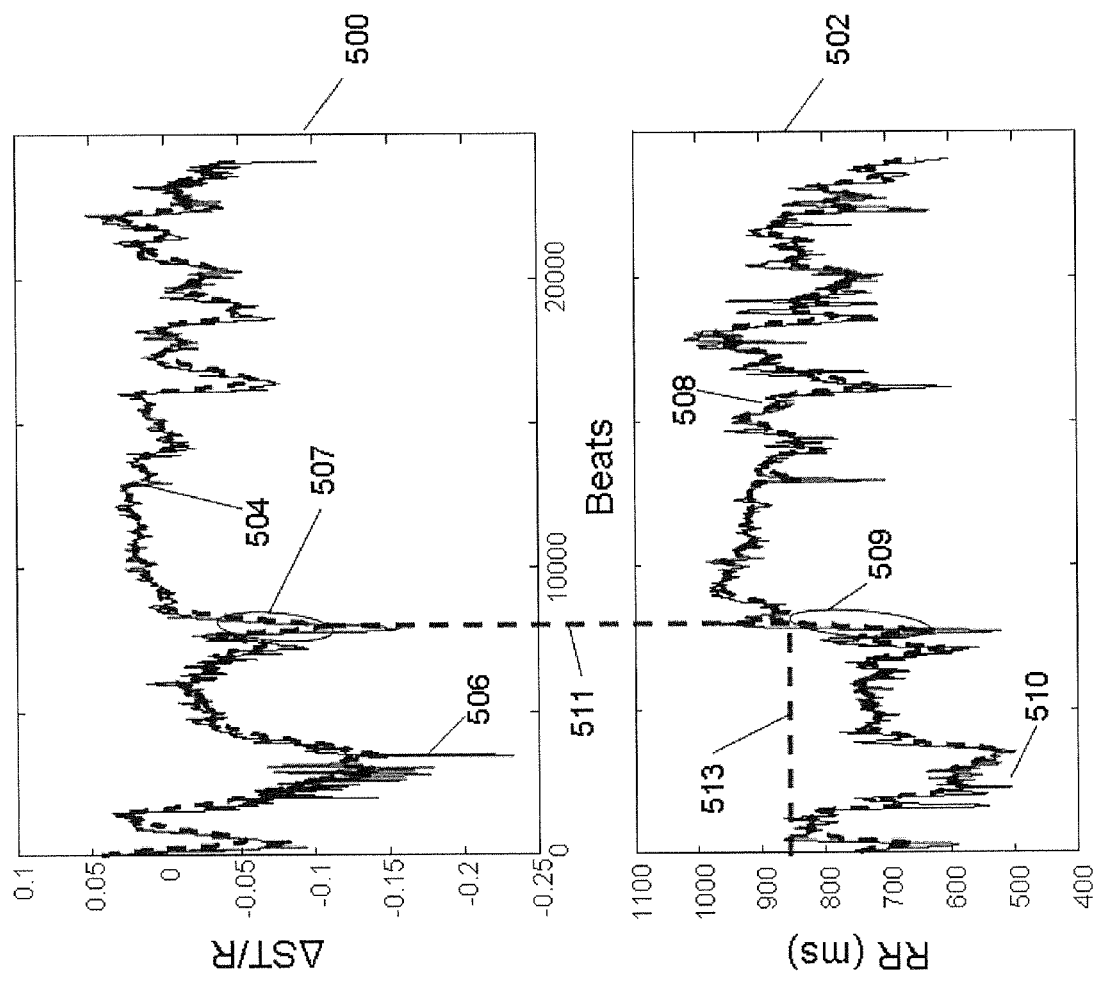
FIG. 3 shows plots of ST segment deviation and RR interval computed from publicly available Holter monitor recordings.

FIG. 3 shows plots 500 and 502 of ST segment deviation and RR interval computed from publicly available Holter monitor recordings. (Patient 7 of the European ST database.) In plot 500, ST segment deviation is measured at the J point relative to the QRS onset point. In the plots 500 and 502, solid lines 506 and 510 respectively show time series data filtered to remove all but very high frequency signal components. The filtering was performed with exponential averaging. The dashed lines tracings 504 and 508 were low pass filtered, again with exponential averaging.

Figure 4:
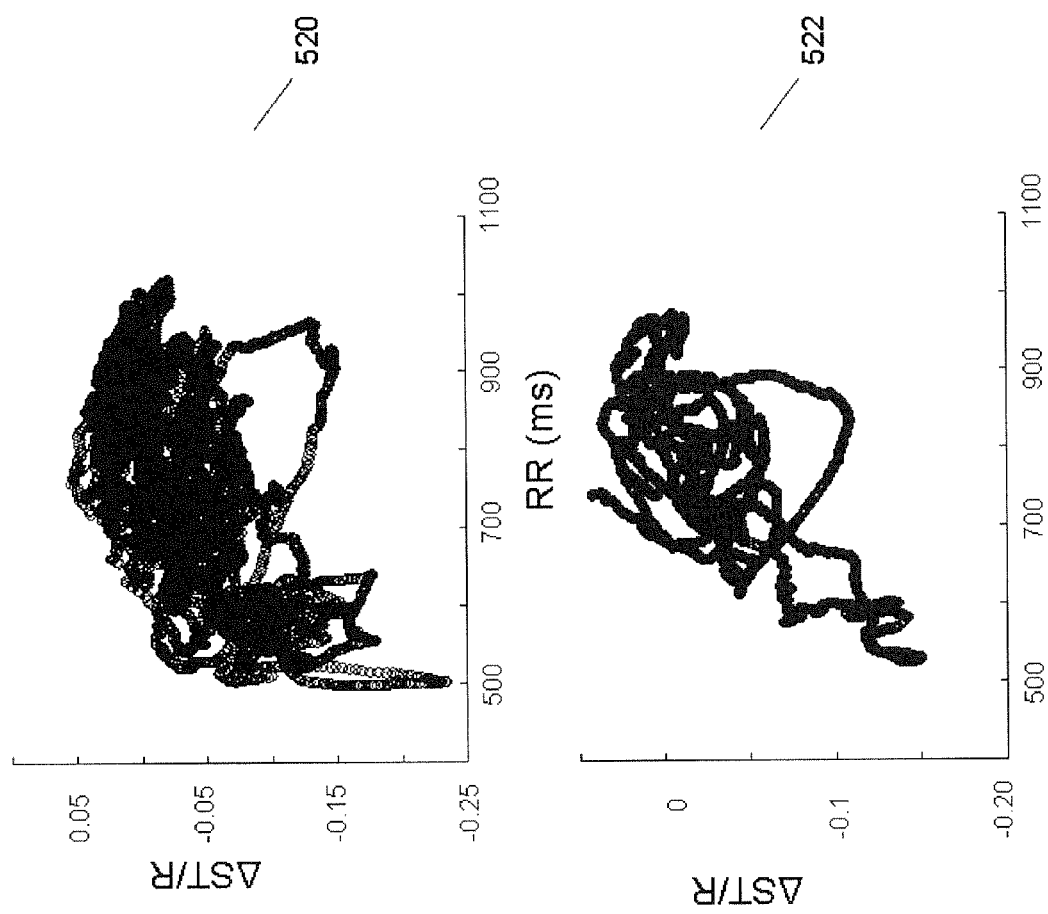
FIG. 4 shows two scatter plots of ST and RR signals corresponding to different filters applied to the ST/RR data.

The high frequency signal components arise from both noise in the measurement process and from physiological causes. Whatever the cause, generally, the higher frequency components of the ST and RR signals are less correlated than the lower frequency components, as is indicated by plots 520 and 522 in FIG. 4.

Plot 520 is a scatter plot of ST vs. RR of the higher frequency tracings 506 and 510 in FIG. 3 while plot 522 is a scatter plot of ST vs. RR of the lower frequency tracings 504 and 508 in FIG. 3. The correlations coefficients associated with the higher and lower frequency scatter plots 520 and 522 are 0.65 and 0.76, respectively, which indicates that the lower frequency data has a higher correlation. This higher correlation in plot 522 is associated with a reduced dispersion of the ST data for a given RR interval, especially at low RR intervals (i.e. higher heart rates).

From the standpoint of detecting a cardiac abnormality, the reduced dispersion associated with plot 522 is preferable. In particular, if a cardiac abnormality causes a persistent ST change that is outside of the scatter plot data of plot 522 but inside the scatter plot data of plot data of plot 520, the abnormality may be detected if the plot 522 serves as the definition of normal. Conversely, if the plot 520 serves as normal, the ST data associated with the abnormal event is less readily distinguishable from the normal data in plot 520.

Figure 5:
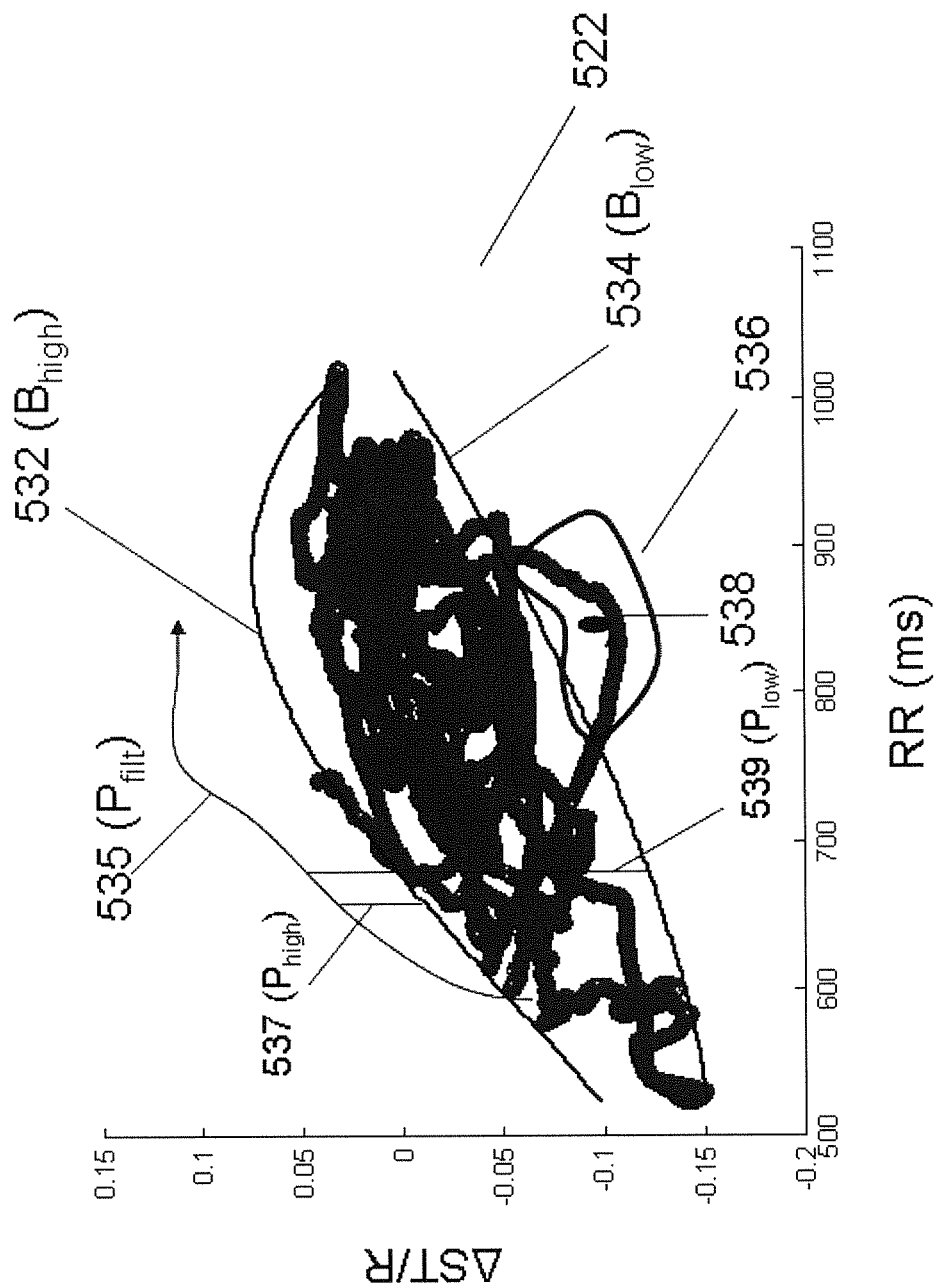
FIG. 5 shows the bottom plot from FIG. 4 along with boundary curves.

A method for distinguishing normal from abnormal data will now be described with reference to FIG. 5 and subsequent figures. FIG. 5 shows plot 522 (FIG. 4) along with boundary curves 532 and 534, labeled $B_{high}$ and $B_{low}$ respectively. ("B" stands for band and high and low stand for the expected normal high and low values of the parameter at a given RR interval.) These curves were generated (with Matlab's fminsearch routine) by fitting cubic polynomials to the upper and lower data points in the plot 522, excluding data points 536, and moving the resulting curves higher and lower respectively by a small amount.

The data 536 was excluded because it represents a period of rapid heart rate recovery that was associated with a decrease in the ST segment level. The arrows show the ST vs. HR trajectory associated with data 536; the RR interval rapidly increased (heart rate rapidly slowed) while the ST segment decreased up until an RR interval of approximately 880 ms, when it finally began to recover toward more normal (less negative) values.

FIG. 3 helps show the relationship between the data 536 and the patient's activity. The portion 509 of the RR plot 502 (FIG. 3) represents a period within which the patient's heart was rapidly slowing down. The associated portion 507 of the ST plot 500 shows that the ST value reaches its (local) minimum value of approximately −0.1 when the RR interval is approximately 850 ms, during the midst of the rapid heart rate decrease. (The intersection of RR=850 ms line 513 with the vertical line 511 helps to pinpoint the ST value associated with this RR interval.)

If data 536 was considered the lower bound of normal (between RR intervals of approximately 790 ms to 900 ms), instead of being excluded from consideration as normal data, then persistent ST changes associated with a truly abnormal cardiac condition would be difficult to distinguish from normal. For example, assume a persistent ST shift of −0.1 at an RR interval of 850 ms as indicated by marker 538. If the 536 data marked the lower boundary of normal, than the condition associated with marker 538 would not be distinguishable from normal.

Since $B_{low}$ (534) excludes the data in 538, in situations where the heart rate recovers rapidly, a normal ST vs. HR trajectory might fall below $B_{low}$; the data 536 is an actual example of this type of trajectory. To avoid a false positive detection in such cases, as will be further described below, the RR trajectory is examined. If the RR trajectory indicates that the person is currently involved in a period of rapid heart rate recovery, the ischemia tests that would otherwise be performed are suspended.

Alternatively, the ischemia tests could be modified to take into account the rapid heart rate decrease; the ST/HR trajectory during rapid heart rate increase could be indicative of a heart abnormality. In particular, such a test may involve examination of the slope of the ST/HR curve during recovery. However, in the preferred embodiment, only steady heart rates or gradually changing heart rates are used to detect a cardiac abnormality.

In order to track whether a trajectory is normal or abnormal, the preferred inventive method involves the calculation of two parameters, $P_{high}$ and $P_{low}$, which correspond to the difference between a trajectory's actual parameter value and the $B_{high}$ and $B_{low}$ bands respectively. For example, trajectory 535 shows a possible development of ST elevation upon recovery from exercise. This ST trajectory is labeled as $P_{filt}$, which represents a filtered parameter value, as will be further described with respect to the flowchart in FIGS. 7a and 7b. For purposes of illustration, $P_{high}$ and $P_{low}$ are represented by the vertical distance bars 537 and 539 at single points but it will be appreciated that $P_{high}$ and $P_{low}$ are each calculated throughout the entire trajectory 535.

FIG. 6 shows an example of a $P_{low}$ plot 602 that was computed with the data associated with the FIG. 3 tracings and the $B_{high}$ and $B_{low}$ bands from FIG. 5. The instances where $P_{low}$ falls below 0 correspond to times when the ST segment (at a given RR) falls below $B_{low}$. Plot 600 represents the value of the slope of the RR curve 502 (FIG. 1). The manner of computing the slope, labeled ΔRR in FIG. 6, will be described below. When ΔRR is positive, the (averaged) heart rate is decreasing. When ΔRR is above a certain threshold, say 0.075, the heart rate is decreasing to the point where it may be desirable to turn off ischemia detection due to the possible effects of hysteresis. These points are indicated by the dots in plot 602. The data pointed to by 604 corresponds to the hysteresis data 536 from FIG. 5). By removing periods of rapid heart rate decrease from consideration from ischemia detection, false positives are avoided, as indicated by the lack of any $P_{low}$ value less than 0 (i.e. below $B_{low}$) other than the rapid recovery data associated with the red dots.

The above described an example of a negative ST vs. HR hysteresis. For a given individual and electrical lead, the hysteresis may be positive or there may not be hysteresis.

Although the above description pertained to the association between ST segment and heart rate, a similar if not identical analysis applies to T wave amplitude and QT interval (or related durations such as ST segment duration as measured, for example, from the J point to the peak of the T wave).

Detection Flowchart

Figure 7A:
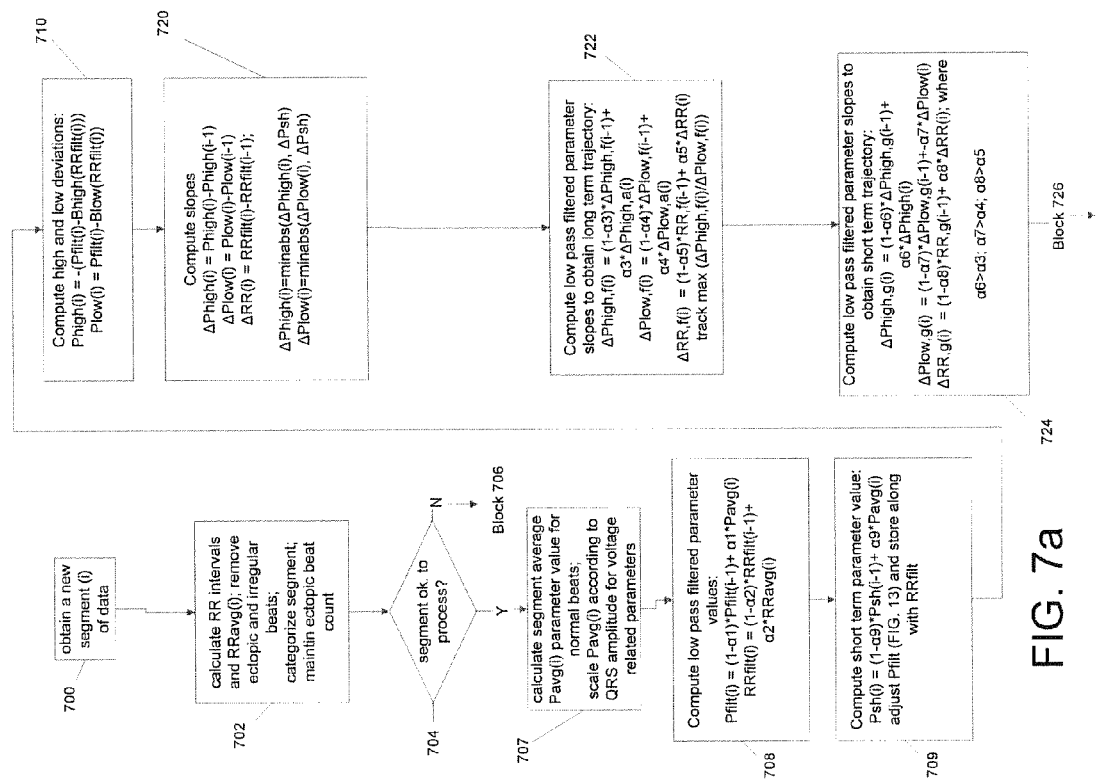
FIGS. 7a and 7b are a flow chart of the preferred method of detecting a cardiac event based o on the values of a heart rate dependent parameter.
Figure 7B:
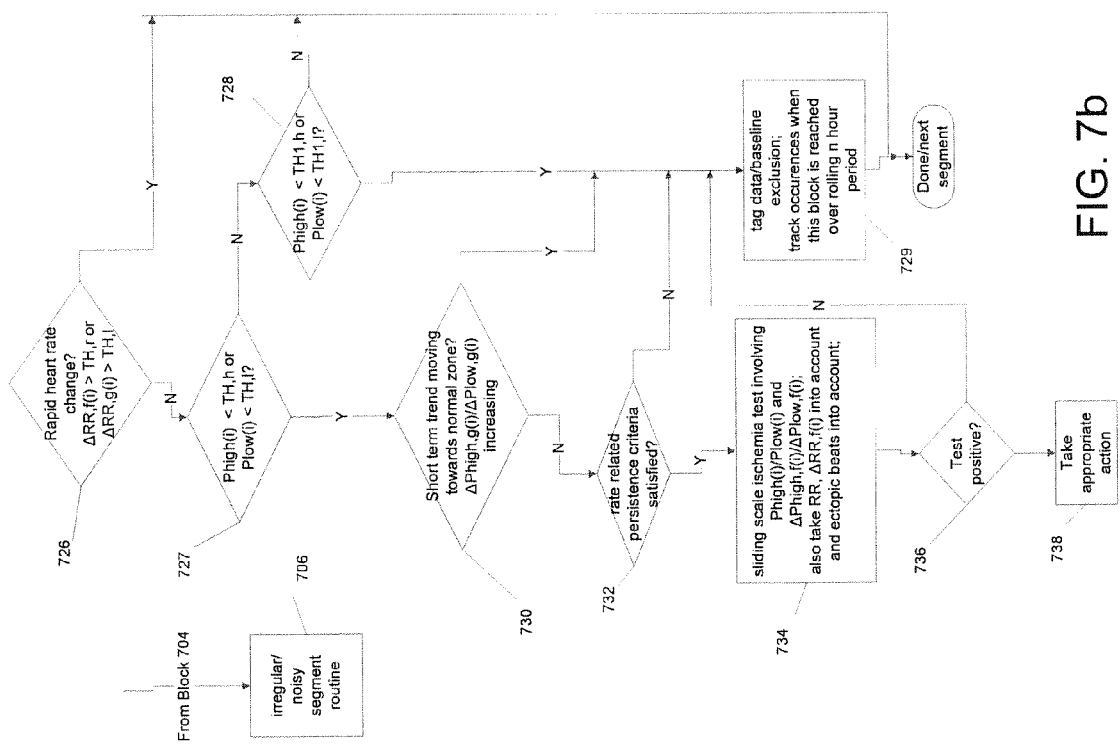

FIGS. 7a and 7b are a flowchart that implements the methodology described above. In block 700, a new segment of data is acquired. The segment is labeled as segment "i"; "i" will also be used to label various other parameters that are time indexed. In the preferred embodiment, the time interval between successive segments decreases upon detection of a parameter change indicative that a cardiac event may be occurring. (See U.S. patent application Ser. No. 11/594,806, filed November, 2006, entitled "System for the Detection of Different Types of Cardiac Events".) Intra-segment time also preferably decreases when the heart rate exceeds a certain threshold.

In the preferred embodiment, the intra-segment duration does not affect the calculation of various moving/exponential averages, which will be described below. In an alternative embodiment, the averaging weight given to a current segment may decrease (e.g. linearly) with decreasing intra-segment duration.

In block 702, ectopic and irregular beats are detected and excluded from consideration. The RR interval each beat not adjacent to an ectopic beat is calculated and then used to compute the segment's average RR interval, $RR_{avg}(i)$. Other measures may be employed to distinguish ectopic/irregular beats from normal ones. Each beat may be compared with the segment's average max/min QRS slopes; ectopic beats are likely to have larger max slopes. T wave amplitude may also be considered in combination with QRS slope: e.g., if a beat's max slope is 30% greater than the segment's average and the T wave amplitude is 30% less than the segment's average, the beat may be classified as ectopic.

Other fiducials may be employed, including some that are independent of the magnitude of the ECG waveform, such as the duration between the maximum and minimum QRS slopes. If this fiducial is significantly different than normal for most or all of a segment's beats, an abnormal rhythm may be occurring that does not manifest itself through an RR interval analysis. (An example of such a rhythm is an idiopathic ventricular rhythm.) Another possible fiducial of this sort is the duration between maximum and minimum QRS potentials.

If a segment has too many ectopic beats, is characterized by a too high or a too low heart rate, or is otherwise irregular, it may be appropriately tagged as described in the '806 application. The number of ectopic beats is also counted and the frequency of ectopic beats is also computed. As will be described with reference to block 734 and as described in U.S. patent application Ser. No. 11/889,752, entitled "System and Methods for Detecting Ischemia With a Limited Extracardiac Lead Set", tests for ischemia may be based both on ectopic beat frequency and other parameters (e.g. ST deviation).

If the segment is too irregular/noisy to analyze for parameter values (e.g. ST deviation), or should otherwise generate an alarm (e.g. high heart rate, serious arrhythmia), block 704 passes control to block 706, which determines an appropriate response. One possible response is to reanalyze the segment with different QRS detection parameters to ensure that the irregularity of the segment is real and not related to processing. If the segment is simply too noisy, then block 706 must select a parameter value $P_{filt}$ for the segment because other routines require a $P_{filt}$ value. One possibility is to select the $P_{filt}$ as the normal, heart rate corrected value (if heart rate can be determined) or equal to an average of the previous and subsequent segments. If there is a string of noisy segments, a flag may be set to suspend all cardiac event detection until normal, noise free processing is resumed.

If the segment is not too irregular to process, block 704 passes control to block 707, which calculates the average parameter value for various parameters is computed for all beats not adjacent to an ectopic beat. These parameters include ST deviation, T wave amplitude, ST duration (QRS onset to T wave peak), maximum and minimum QRS slopes, minimum ST segment value, and the duration between the QRS offset and the first sample of the ST segment that exceeds the band (QRS onset point) value. Also, with regard to the final upstroke or downstroke of the QRS (i.e. the final peak of the QRS to the QRS offset point), an additional parameter is the duration between the maximum slope of the upstroke or downstroke and the time the slope reaches a specified percentage (e.g 40%) of this value. For all of these parameters, the average segment parameter value $P_{avg}(i)$ is computed by summing the raw parameter values and dividing by the corresponding number of beats.

All voltage related parameters (other than QRS peak-to-peak voltage) are scaled according to the amplitude of the average QRS peak-to-peak voltage. The type of scaling that is applied will depend on the empirically established relationship between QRS peak to peak voltage and other ECG features. The goal of the scaling is to reduce the variability of the ECG features. Taking ST-deviation as an example, the inventor's work as shown that at least in some leads, the dispersion of ST-deviation is minimized by scaling only if the QRS peak to peak voltage ($QRS_{pk}$) is less than a certain threshold QRSpk,m. In particular, the scaling function takes the value of $=1+a*(max(QRS_{pk,m}-QRS_{pk}),0)$, where both $QRS_{pk,m}$ and "a" are chosen so as to minimize dispersion of ST-deviation.

The rationale for scaling only if $QRS_{pk}$ is less than $QRS_{pk,m}$ is that different processes may govern whether $QRS_{pk}$ is greater or less than $QRS_{pk,m}$. In particular, $QRS_{pk,m}$ may represent the minimum $QRS_{pk}$ when a person is upright, in which case $QRS_{pk}$ values greater than $QRS_{pk,m}$ represent noise in the QRS measurement process that does not greatly affect the ST-deviation measurement process. Conversely, if $QRS_{pk}$ is less than $QRS_{pk,m}$, the cause may be a body position shift that causes an overall decrease in signal amplitude. In this case, it is necessary to scale up the amplitude.

Control passes to block 708, which computes low pass filtered values of the parameters $P_{avg}(i)$ and $RR_{avg}(i)$. This low pass filtering tends to remove noise (physiological and otherwise) as previously described with reference to FIG. 3. The preferred filtering involves the computation of exponential averages: $P_{filt}(i)=(1-\alpha1)*P_{filt}(i-1)+\alpha1*P_{avg}(i); RR_{filt}(i)=(1-\alpha2)*RR_{filt}(i-1)+\alpha2*RR_{avg}(i)$. The optimal $\alpha1$ and $\alpha2$ values will depend on segment duration and inter-segment interval and possibly patient specific factors. Generally, with a 10 second segments and a 30 second inter-segment interval, setting $\alpha1$ and $\alpha2$ values to 0.2 produced good results.

As a precursor to computing the filtered values, $P_{avg}(i)$ may first be compared to a threshold to determine if is physiologically reasonable (e.g. an (i) value of 100 ms is not reasonable). If not, $P_{avg}(i)$ may be set to $P_{filt}(i-1)$ and/or the segment may be reanalyzed with different parameter detection parameters to determine whether the outlying segment parameter value was caused by processing. Reanalysis of the segment with different parameter detection values helps to provide feedback for those values. A possible example of a parameter detection value is the maximum slope that will be considered acceptable for a QRS onset point. (Checks on $RR_{avg}$ were already described with respect to block 704.)

Control passes from block 708 to 709, which is similar to block 708 except that short term $P_{sh}(i)$ parameter values are calculated that represent the average value of the parameter over approximately 1-2 minutes. As will be further described below, the difference between changes in the short term values $P_{sh}$ and the long term values $P_{filt}$ determines how the average change of the parameter is calculated in block 720.

Block 709 also adjusts $P_{filt}$ to account for body position shifts. This adjustment process for $P_{filt}$ will be described with reference to FIG. 13. The adjusted $P_{filt}$ is then stored so that it may be used to obtain the bounds $B_{high}$ and $B_{low}$, as will be described in the section entitled "Obtaining Bounds".

Control passes from block 709 to 710, which computes high and low deviations $P_{high}(i)=-(P_{filt}(i)-B_{high}(RR_{filt}(i)))$ and $P_{low}(i)=P_{filt}(i)-B_{low}(RR_{filt}(i))$, where $B_{high}$ and $B_{low}$ are heart rate dependent high and low bands, respectively (see FIG. 5, which also shows examples of $P_{high}$ and $P_{low}$ for the ST trajectory $P_{filt}$). If body position data is available, so that there are $B_{high}$ and $B_{low}$ curves for different body positions then the appropriate $B_{high}$ or $B_{low}$ is selected. More generally, there may be different $B_{high}$ and $B_{low}$ curves for different patient states (e.g. sleeping, exercising) and also for whether the heart rate is rapidly increasing or decreasing. Having different patient state depending $B_{high}$ and $B_{low}$ may be more important for some parameters (e.g. ST segment duration) than others (e.g. QRS duration).

Control passes from block 710 to block 720, which computes the changes in parameter values over time (i.e. slopes): $\Delta P_{high}(i)=P_{high}(i)-P_{high}(i-1)$, $\Delta P_{low}(i)=P_{low}(i)-P_{low}(i-1)$, and $\Delta RR(i)=RR_{filt}(i)-RR_{filt}(i-1)$. In an alternative embodiment, there is only one variable $\Delta P$ that tracks the change in $P_{filt}$ (instead of two, $\Delta P_{high}(i)$ and $\Delta P_{high}(i)$); $\Delta P$ is calculated by correcting the actual change in parameter value $P_{filt}(i)-P_{filt}(i-1)$ by the expected change, which is determined e.g. by the average of the $B_{high}$ and $B_{low}$ curves. For example, if there is a linear relationship between ST deviation and RR interval characterized by a slope M, and the actual change in ST deviation was −5% when the RR interval changed from 1000 ms to 700 ms, then the corrected ST deviation is −5%-(M*−300 ms).

In yet another alternative embodiment, the above described heart rate correction is performed in the context of different filtering schemes. For example, a heart rate corrected ST-deviation time series may be filtered in a manner described in the prior art for non-heart rate corrected ST-deviation. In other words, heart rate corrected ST deviation (or other parameter) may be input into prior art filters applied to uncorrected ST deviation. Furthermore, heart rate correction may be applied to derive heart rate corrected ST deviation reference levels; non-heart rate corrected ST deviation reference levels, and the application of those references to ischemia detection, is described by Smrdel and Jager. (Automated detection of transient ST-segment episodes in 24 h electrocardiograms. *Med Biol Eng Comput.* 2004; 42(3):303-11.)

If $\Delta P_{high}$ and $\Delta P_{low}$ have greater magnitude than $\Delta P_{sh}=P_{sh}(i) P_{sh}(i-1)$, they are reduced to the magnitude of $\Delta P_{sh}$. (The minabs(a,b) operation in FIG. 7 indicates that a or b is selected, whichever has a smaller absolute value.) This adjustment is performed to prevent sharp changes in a raw parameter value from appearing as long term changes due to the characteristics of exponential average filters. For example, if ST deviation changes from a steady state value of 0% to a steady state value of 5% between consecutive segments, the change is likely due to a body position shift. The exponential average filter output $P_{filt}$ will gradually change from 0% to 5%, say over the course of 3 minutes. During this time, the average change in $P_{filt}$ (i.e. $P_{filt}(i)-P_{filt}(i)$) will also gradually increase. However, since it is desired to distinguish the gradual parameter changes induced by ischemia from such abrupt changes, this abrupt 5% should be attenuated or removed, so that the average change in $P_{filt}$ (more particularly $\Delta P_{high}$ and $\Delta P_{low}$) is low. (One specific aim of the present invention to detect acute ischemia when the average change in $P_{filt}$ ($\Delta P_{high}$ and $\Delta P_{10}$) is relatively large. By limiting the change in $\Delta P_{high}$ and $\Delta P_{low}$ to the actual short term change $\Delta P_{sh}$, which is small when the parameter value in question has reached a steady state, abrupt changes are prevented from appearing as gradual ones, which would otherwise occur due to the delayed response of the long term exponential average filter.

An alternative to limiting changes in $\Delta P_{high}$ and $\Delta P_{low}$ to the magnitude of $\Delta P_{sh}$ is to reduce $\Delta P_{high}$ and $\Delta P_{low}$ or set them to 0 if the difference between $P_{filt}$ and $P_{sh}$ is too large.

The above mentioned procedure (limiting parameter changes to $\Delta P_{sh}$ also helps to prevent heart rate related effects, namely hysteresis, from causing changes to the average change in $P_{filt}$ (due to corrections for RR interval changes) when the actual change in the parameter ($\Delta P_{sh}$) is small.

Block 720 passes control to block 722, which computes low pass filtered parameter slopes to obtain long term trajectories of parameters, including heart rate (RR interval): $\Delta P_{high,f}(i)=(1-\alpha3)*\Delta P_{high,f}(i-1)+\alpha3*\Delta P_{high,a}(i)$, $\Delta P_{low,f}(i)=(1-\alpha4)*\Delta P_{low,f}(i-1)+\alpha4*\Delta P_{low,a}(i)$, and $\Delta RR_f(i)=(1-\alpha5)*RR_f(i-1)+\alpha5*\Delta RR(i)$. A good value for $\alpha3$, $\alpha4$ and $\alpha5$ is 0.2. Ischemia tests (block 734) are based directly on the values of these long term trajectories as well as the parameter values themselves (e.g. $P_{low}$, an example of which is shown in plot 602 in FIG. 6). Furthermore, the heart rate (RR) parameter also is examined to determine whether an ischemia test is applied to particular data; more generally, the $\Delta RR$ parameter (an example of which is shown in plot 600 in FIG. 6) may be examined to determine the type of ischemia test to apply to certain data. For example, with reference to FIG. 5, when the $\Delta RR_f(i)$ parameter exceeds a threshold, data associated with trajectory 536 is excluded from the normal ischemia test. A separate type of ischemia test, based upon changes in parameter values associated with recovery from exercised, may be applied to this data. This separate test may be applied soon after the trajectory 536 is computed or may involve the combination of trajectory 536 with other data to determine, e.g., whether chronic ischemia is worsening.

Block 722 also keeps track of the maximum value of $\Delta P_{high,f}$ and $\Delta P_{low}$ over a certain period, preferably 5-10 minutes for reasons that will be discussed with respect to block 734.

Control passes to block 724, which computes short term averaged slopes of the parameters for which long term slopes are computed in block 724. In an alternative embodiment, the second derivative of the long term slope may be computed to assess the extent short term parameter value/RR trajectories. All of the $\alpha$'s in the exponential averaging functions in block 724 are greater than the corresponding $\alpha$'s in block 722, so that block 724 produces short term averaged slopes that correspond to the recent trend in the parameters. A good value for all of the $\alpha$'s in block 724 is 0.7. As will be discussed further in connection with block 730, short term parameter trends may be examined to help avoid false positives. In particular, if a parameter's value and its long term trend both indicate acute ischemia but the parameter is already starting to change back towards its normal values, as indicated by the short term trend, it may be desirable to avoid detecting the event (or at least to take an action not indicative of an emergency).

Otherwise, in block 726, the routine determines whether a rapid heart rate change is occurring by comparing both the long and short term heart rate trends to respective thresholds. It is preferable to examine both long and short term heart rate trends for two, complementary reasons. First, the short term trend may indicate the heart rate is steady but the long term trend has "memory" of a recent transition from higher rates to lower rates, and the heart may therefore still be in recovery mode regardless of the value of the short term heart rate trend. Second, the short term trend may indicate the heart rate is changing but the long term trend either has not had enough time to register the change or is moving through an inflection point. If either the short term or long term trend exceeds its associated threshold, then the routine exits. In an alternative embodiment, current heart rate vs. parameter trajectory may be always stored, or selectively stored depending on the values of $P_{high}(i)$ and $P_{low}(i)$.

Finally, in the case where the heart rate rapidly changes from increasing to decreasing (or vice versa), there can be a short period of time just after the heart rate direction change when the values of both the short term or long term trends are small. To ensure that this time period is tagged as a rapid heart rate change period, the routine determines whether the long term heart rate trend has reached a maximum or minimum that exceeds a threshold; for a set period of time after the maximum or minimum, a rapid heart rate change will be assumed.

If neither short term nor long term heart rate trends are indicative of changes, then control transfers to block 727. In block 727, the high and low parameter deviations $P_{high}(i)$ and $P_{low}(i)$ are compared to corresponding thresholds. If neither deviation is below its associated threshold, the routine passes control to block 728, where $P_{high}(i)$ and $P_{low}(i)$ are compared to corresponding thresholds that are smaller (less negative) than the thresholds in block 727. If $P_{high}(i)$ or $P_{low}(i)$ are less than these smaller thresholds, it may be desirable to exclude the data from calculation of bands $B_{high}$ and $B_{low}$, as will be discussed further with respect to FIG. 9 and/or to detect a different type of cardiac event if such the change ($P_{high}(i)$ or $P_{low}(i)$<block 728 thresholds) persist. Block 729 handles the processing associated with band exclusion and/or different event detection, as will be further described with respect to FIG. 9.

If neither $P_{high}(i)$ nor $P_{low}(i)$ is less than its block 728 threshold, the routine exits.

Returning to block 727, if either $P_{high}(i)$ or $P_{low}(i)$ is below its associated threshold, the routine passes control to block 730. As mentioned, block 730 checks whether the parameter values are moving toward normal, in which case the routine passes control to block 729. Again, in an alternative embodiment, the heart rate vs. parameter curve may be stored. If these parameter values are not moving toward normal, the control passes to block 732, which applies persistence criteria to $P_{high}(i)$ or $P_{low}(i)$, which ever is below its threshold. Because $P_{high}(i)$ and $P_{low}(i)$ are based on long term averaged parameter values, in some sense $P_{high}(i)$ and $P_{low}(i)$ reflect persistent changes. Indeed, in an alternative embodiment, at relatively low heart rates that have been steady (long term $\Delta RR$ value is very small) and small $\alpha 1$ (see block 708), no additional persistence criteria is applied to $P_{high}(i)$ and $P_{low}(i)$. In the preferred embodiment, persistence criteria are heart rate dependent; at higher heart rates, it is preferably to require $P_{high}(i)$ or $P_{low}(i)$ to stay below threshold for a relatively longer period of time before an ischemic event is detected. This waiting period is preferably programmable but a good initial choice is five minutes. (The persistence criteria in block 732 and the short term trend test in block 730 overlap somewhat but tend to reinforce each other.)

If the rate related persistence criteria are not satisfied, the routine passes control to block 729. Otherwise, control passes to block 734, which applies an ischemia test $P_{high}(i)$ or $P_{low}(i)$, whichever is below threshold, and the corresponding averaged slope $\Delta P_{high,f}(i)$ or $\Delta P_{low,f}(i)$. One possible test is an "or" type test that separately examines the absolute value of the parameter $P_{high}(i)$ or $P_{low}(i)$, the averaged slope $\Delta P_{high,f}(i)$ or $\Delta P_{low,f}(i)$ and some combination of parameter and slope. For example, if any of the following is satisfied, the ischemia test is positive:

(1) small RR, $\Delta_f(i)$ and low RR: (a) $P_{high}(i)$ or $P_{low}(i)$<−20% (R/S wave height); or (b) $P_{high}(i)$ or $P_{low}(i)$<−10% (R/S wave height) and corresponding $\Delta P_{high,f}(i)$ or $\Delta P_{low,f(i)}$<−3% (R/S height)/min;

(2) moderate $\Delta RR_{,f}(i)$ or moderate RR: (a) $P_{high}(i)$ or $P_{low}(i)$<−30% (R/S wave height); or (b) $P_{high}(i)$ or $P_{low}(i)$<−20% (R/S wave height) and corresponding $\Delta P_{high,f}(i)$ or $\Delta P_{low,f}(i)$<−3%(R/S height)/min;

(3) substantial ectopic activity (e.g. >15 ectopic beats/min over at least 2 minutes) and: (a) $P_{high}(i)$ or $P_{low}(i)$<−10% (R/S wave height); or (b) $\Delta P_{high,f}(i)$ or $\Delta P_{low,f}(i)$<−2% (R/S height)/min.

Note that if −10% (R/S wave height) is set as the threshold in block 726, then the 1(b) and 2(b) tests above need only involve an examination of $\Delta P_{high,f}(i)$ or $\Delta P_{low,f}(i)$.

As mentioned with respect to block 722, maximum values of $\Delta P_{high,f}(i)$ and $\Delta P_{low,f}(i)$ are maintained for a certain period. These maxima, if different than the current $\Delta P_{high,f}(i)$ or $\Delta P_{low,f}(i)$ are used in the above mentioned ischemia tests. The maximum $\Delta P_{high,f}(i)$ or $\Delta P_{low,f}(i)$ are appropriate in the case where a parameter change plateaus after a few minutes but before the persistence criteria (block 732) are met. During the plateau, $\Delta P_{high,f}(i)$ or $\Delta P_{low,f}(i)$ may decrease below values indicative of an ischemic event. Yet the persistence of the parameter change during the plateau indicates an ischemic event is occurring, and the maximum $\Delta P_{high,f}(i)$ or $\Delta P_{low,f}(i)$ values (before the plateau), combined with persistence of the absolute parameter change $P_{high,f}(i)$ or $P_{low,f}(i)$ indicates ischemia.

If any test is positive, block 736 transfers control to block 738, which involves the generation of an appropriate action, which may involve generation of different levels of alarms/messages to the patient and/or third parties, storage of the data associated with the event, etc.

Figure 8:
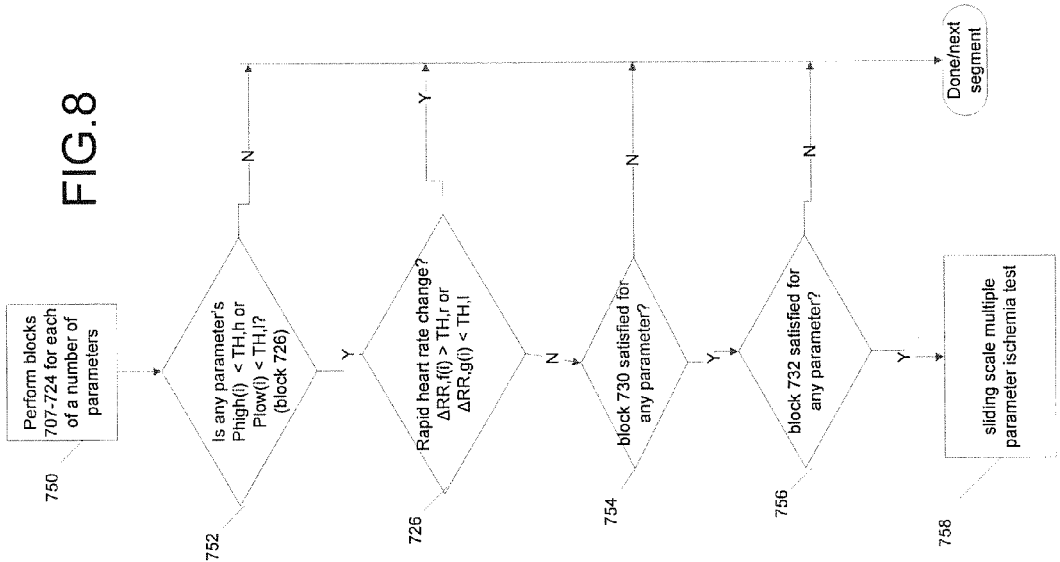
FIG. 8 is a flow chart that shows how to apply the single parameter method of FIGS. 7a and 7b to multiple parameters.

For purposes of clarity, FIGS. 7a and 7b has been described with reference to a single parameter (and heart rate). Preferably, the detection of acute ischemia (and other cardiac events) involves a number of parameters. FIG. 8 shows one possible way to adapt FIGS. 7a and 7b to a multiple parameter detection scheme that can involve more than one lead. In block 50, all of the individual steps in blocks 707-724 (FIG. 7) are performed for each parameter of interest. In block 752, the threshold test of block 726 is applied separately to each parameter—if any of the parameters is underneath its threshold, then control passes to block 728, which is from FIG. 7b. Otherwise, the routine exists.

If block 726 determines a rapid heart rate change has not occurred, control passes to block 754, which applies the block 730 test separately to each parameter. Again, if any parameter satisfies this test, control passes to block 756, which separately applies the block 732 test to each parameter. If any parameter satisfies this test, control passes to block 758, which performs a multiple parameter cardiac event detection test.

In an alternative embodiment, $P_{filt}$ may be calculated so that it represents a short term value (e.g. the average parameter value over 1-2 minutes instead of a longer period). In this case, the change in $P_{filt}$ (block 720) may not be allowed to exceed changes that are larger than the slopes (changes) likely to be produced by ischemia. Block 722 would follow by producing averaged values of these filtered slopes. The combination of removing/attenuating large slopes and averaging of the resulting filtered slopes (block 722) results in averaged, gradual parameter changes over time. If a change in a parameter is occurring gradually (meaning over the span of minutes), as is the case of acute ischemia, each individual segment-by-segment change (slope) will pass unattenuated and form part of the average of the block 722 filter. With appropriate choice of filtering coefficients, after a few minutes of consistent changes, the output of the block 722 will become relatively large.

Conversely, sharp changes caused by events such as body position shifts will be removed or attenuated, so that the output of the block 722 filter after such events is small. In this manner, the combination of a magnitude based filter and block 722 combine to enable gradual changes in a parameter value from more rapid changes that are unlikely to be caused by acute ischemia.

With appropriate choice of coefficients, such a filter and 722 can produce averaged parameter changes over longer time periods, which may be suitable for tracking conditions other than acute ischemia.

In an alternative embodiment, the filter in block 721 may be adaptive, so that if a string of consecutive large slopes that would otherwise be removed, the filter coefficients are modified to allow these larger slopes to pass. Such a string of consecutive large slopes can not be caused by body position changes and may have a physiological cause, e.g. acute ischemia may cause larger changes per unit time than the filter was originally configured to accept. (A string of consecutive large changes would cause a relatively large change in the absolute value of the parameter; if a test to determine whether a cardiac event has occurred involves a sliding scale between average slope (block 722 output) and absolute parameter value, then it matters less that the averaged slope produced by block is small, since the large absolute parameter change would trigger detection. However, allowing the attenuation filter to adapt to a string of large slopes is an additional safeguard for detecting the event.

There are two additional alternatives for distinguishing between a transitory large slope (e.g. caused by a body position change) and a string of large slopes (possibly caused by ischemia). First, the length of a string of large slopes may be counted, and result in a positive ischemia test (see block 734) if it exceeds a threshold, i.e. ischemia is detected if a large change is persistent. Second, instead of applying an attenuation filter, large slopes may be included within the average slope calculation (block 722). In this case, a single large slope may cause a transitory increase in the average/filtered slope parameter $\Delta P_{high,f}$), which will rapidly return to small values after the sharp change caused by the single large slope. Thus, to detect a persistent change in slope, $\Delta P_{high,f}(i)$ must remain at a relatively high level for a certain duration; a temporary change in $\Delta P_{high,f}(i)$, such as may be caused by a body position shift, would not result in a positive ischemia test.

Figure 13:
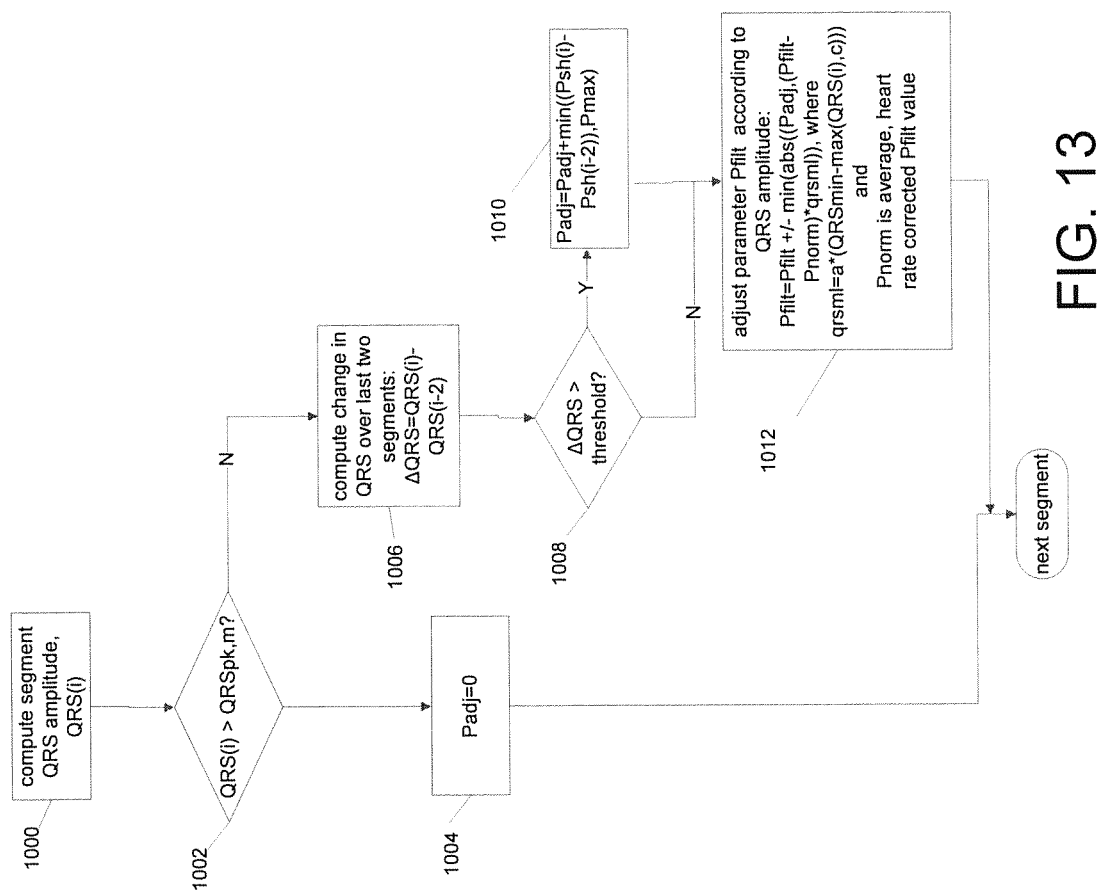
FIG. 13 is a flowchart of the adjustment of parameter values to account for body position shifts.

FIG. 13 is a flowchart of the adjustment of parameter values to account for body position shifts, a routine called from block 721 of FIG. 7a. The routine in FIG. 13 is most pertinent to an embodiment of FIGS. 7a and 7b in which a voltage based parameter (e.g. ST deviation) is adjusted for QRS amplitude although to the extent that there is a positive correlation between QRS amplitude and a time related parameter (e.g. QT interval), the routine in FIG. 13 may be useful. Taking ST deviation as an example, instead of computing absolute ST deviation, in the context of an implantable device in which it is difficult to obtain a calibrated voltage, ST deviation is preferably computed as some function of QRS amplitude. (See, e.g., U.S. Pat. No. 6,609,023 to Fischell et al.) Rather than normalizing ST deviation by R wave amplitude (as described in U.S. Pat. No. 6,609,023) on a beat by beat or segment by segment basis, it may be desirable to normalize R wave amplitude by an average QRS amplitude over a longer period of time (e.g. a day). In this case, if the present invention is applied to body surface of subcutaneous electrodes, it may be necessary to adjust for some types of body position shifts that can cause wholesale decreases in the amplitude of the ECG waveform. The routine in FIG. 13 makes all necessary adjustments.

Turning to the routine, in block 1000, the current segment's average peak to peak QRS amplitude (for normal beats) is computed. QRS(i) may be set equal to this raw value or in noisy situations may be equal to a short term exponential average of the QRS(i) time series. Block 1000 passes control to block 1002, which determines whether the current QRS amplitude is above the threshold $QRS_{pk,m}$ (see discussion of block 707, FIG. 7a). If so, no adjustment to the parameter value is necessary.

If no adjustment is necessary, control passes to block 1004, which results the parameter adjustment variable $P_{adj}$ to 0. Otherwise, control basses to block 1006, which computes the QRS amplitude shift ($\Delta QRS$) over 2 segments (in the case where segments are 10 s and acquired every 30 seconds). It is preferable to examine changes over 2 segments in case a body position shift occurs within a segment. Block 1008 determines whether this shift is greater than a threshold that is the maximum QRS shift that would be expected to be caused by acute ischemia; if the shift is less than the maximum ischemic shift, then the amplitude change may be associated with ischemia, and it is not desirable to adjust the parameter. (In an alternative embodiment, if the smoothness of the change in QRS amplitude indicates acute ischemia is occurring, the parameter could be adjusted in a manner to amplify its changes rather than attenuating parameter changes, which is the role of the routine in FIG. 13.)

If $\Delta QRS$ is greater than the chosen threshold, control passes to block 1010, which changes an adjustment parameter $P_{adj}$ by the size of the parameter shift associated with the presumed body position shift, i.e. ($P_{sh}(i)-P_{sh}(i-2)$), where $P_{sh}$ is a short term average of the parameter (see block 709 of FIG. 7a). The parameter shift is not permitted to exceed a maximum of $P_{max}$, which is the maximum reasonable parameter shift that may be expected in association with a body position shift. If the parameter change is positive or negative then the adjustment in block 1012 is an increase or a decrease, respectively.

Control from either block 1008 or block 1010 passes to block 1012. Note that if the current $\Delta QRS$ is less then the threshold in block 1008, a parameter adjustment may still be necessary due to a past body position shift that is now the current body position. This current body position may be associated with a steady, but lower than normal, QRS. $P_{adj}$ keeps track of the net effect of all of the incremental jumps in parameter value associated with QRS jumps (whether decreases or increases) and serves to adjust the current parameter value regardless of whether the current segment is associated with a QRS jump.

Block 1012 determines the extent of the adjustment as the smaller (in magnitude) of $P_{adj}$ and an adjustment factor that is a function of the difference between the normal (heart rate corrected) parameter value and the current parameter value ($P_{filt}-P_{norm}$). Noise may cause $P_{adj}$ to not accurately reflect the sum of the parameter shifts associated with body position shifts, in which case and adjustment by $P_{adj}$ could occur even when the current parameter value is close to the normal and QRS(i) is close to (but just beneath) normal. The adjustment factor ensures that the adjustments are never larger than appropriate. The adjustment factor is set equal to ($P_{filt}-P_{norm}$)*(a*($QRS_{min}$-max(QRS(i),c))). This ensures that a spurious QRS amplitude below the value of the factor "c" does not cause an over-adjustment. The factor "a" attenuates the adjustment and is preferably chosen empirically by selecting a value that results in a minimum dispersion of $P_{filt}$ across a range of body positions/QRS amplitudes.

Acute ischemia may cause a steady reduction in QRS amplitude. The QRS amplitude is a parameter that is preferably processed according to the scheme described in FIG. 7a and FIG. 7b, excluding the parameter adjustment performed in FIG. 13 to avoid the obvious circularity. If a steady QRS change is occurring, the adjustment of other parameters (e.g. ST deviation) performed in FIG. 13 is preferably turned off, to avoid possible corrections of these parameters toward their normal values (block 1012) when in fact acute ischemia is causing them to become abnormal. (Some miscorrections will already have occurred; in an alternative embodiment, the corrections to parameter values made in block 1012 may be stored for 1-3 minutes and the parameters may be re-corrected accordingly if there is a gradual QRS amplitude change occurring.)

Obtaining Bands $B_{high}$ and $B_{low}$ (see FIG. 5) should be periodically updated to reflect (and detect) changes in a person's cardiovascular condition. $B_{high}$ and $B_{low}$ may be computed every hour for persons expected to experience consistent changes in cardiovascular state; the days after a stent emplacement are an example when such frequent band updating is desired. In more stable patients, band updating every 12 hours may be sufficient. In any event, a band is updated at a particular time based on 24 hours of data prior to that time.

Figure 9:
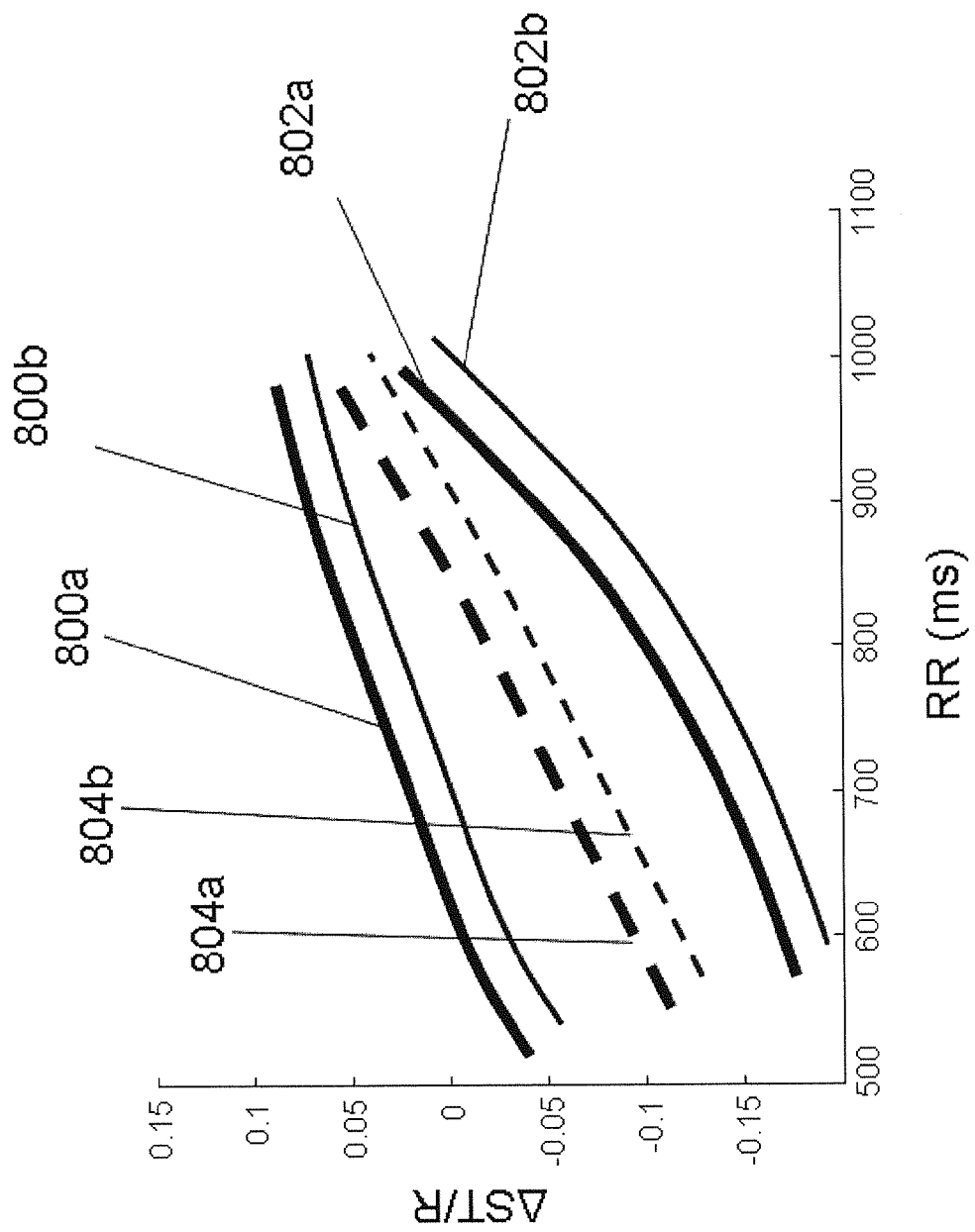
FIG. 9 is a plot that shows an example of computing different high and low parameter bands at different times.

FIG. 9 shows an example of a band update. Curves 800a and 802a represent $B_{high}$ and $B_{low}$ just before a band update whereas curves 800b and 802b represent $B_{high}$ and $B_{low}$ after the update. Curves 804a and 804b represent the average of $B_{high}$ and $B_{low}$ before (804a) and after (804b) the band update and may be used in an alternate embodiment, as will be further described below.

In the example shown in FIG. 9, the parameter values have shifted down during the period in which band data was collected, i.e. 24 hours before the update occurs. If the shift in bands (either 800b compared to 800a or 802b compared to 802a is too great, it may be appropriate to detect a cardiac event.

Figure 14:
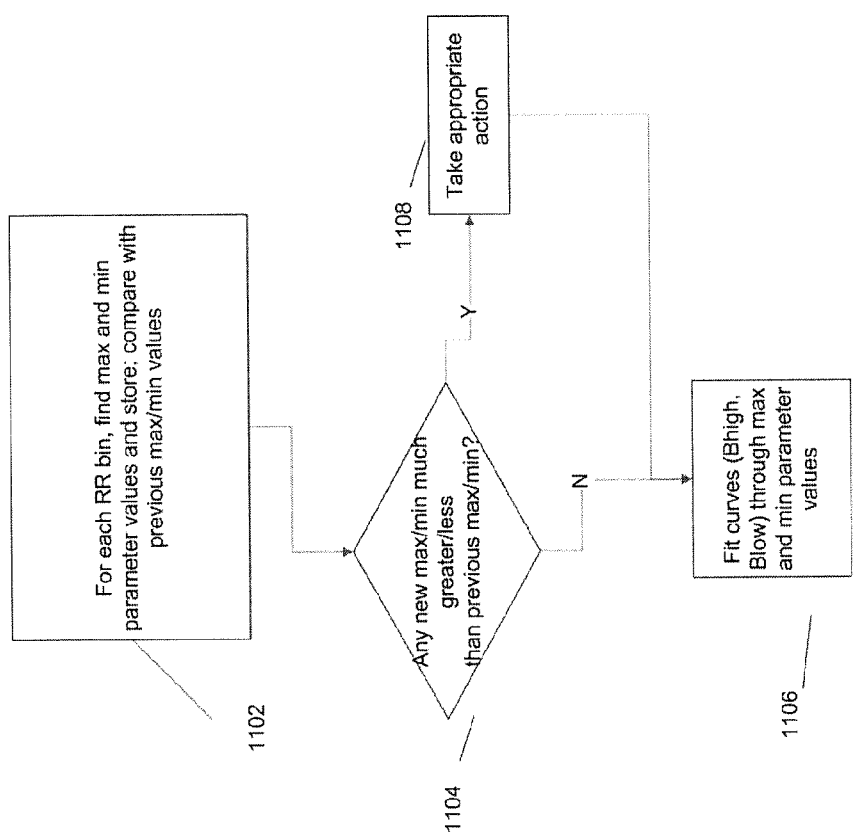
FIG. 14 is a flowchart of a preferred procedure for updating the normal upper and lower bounds of a parameter.

FIG. 14 is a flowchart of a preferred bound update procedure. In block 1002, the $P_{filt}(i)$ data produced by block 708 of FIG. 7, as adjusted by block 721 (and the routine in FIG. 13) but excluding data removed by block 729 of FIG. 7a, is separated into a number of RR bins (e.g. 501 ms-600 ms; 601 ms-700 ms etc.) The exclusion of data by block 729 will be further described below.

Preferably, the RR bins are selected so that no bin encompasses an RR interval with a sharp change in parameter values. Further, for the (smaller) RR intervals associated with larger parameter value changes as a function of changes in RR interval, the bins are preferably finely spaced.

For each bin, the maximum and minimum parameter values are located and compared with the corresponding maximum and minimum values from the previous bound update. If there has been a substantial change in any maximum or minimum parameter value for any RR interval bin, then block 1004 passes control to block 1008, which takes an appropriate action such as generating a "non-emergency" alarm. In any event, in block 1006, $B_{high}$ and $B_{low}$ are computed. In one embodiment, $B_{high}$ and $B_{low}$ are cubic curves that are fit with an optimization procedure through the max/min points. In an alternative embodiment, the maximum and minimum values may be connected by straight lines, so that $B_{high}$ and $B_{low}$ are piecewise linear.

Changes over longer periods of time, not just from one band update to the next, may also result in an event detection. U.S. patent application Ser. No. 10/950,401, filed October 2004, entitled "Implantable System for Monitoring the Condition of the Heart" to Fischell et al. describes storing values of heart rate related parameters over long periods of time and detecting a cardiac event if a change in the average occurs over, e.g., a multi-day period. $B_{high}$ and $B_{low}$ could be stored and evaluated in this fashion. (They could be stored either by discrete $B_{high}$ or $B_{low}$ values at particular RR intervals or indirectly by $B_{high}$ or $B_{low}$ polynomial coefficients, if $B_{high}$ or $B_{low}$ are parameterized by polynomials or in some other fashion.)

In some instances, there may not be data for a particular heart rate range for an update period. For example, a person may be sick in bed, in which case her or his heart rate may stay low, so there is no high heart rate data for that period. In this case, if there has been little band change in the heart rate zone for which data exists, then the updated bands may be set equal to the previous bands. If a band change has occurred in the heart rate zone for which data exists, say a shift downward in the parameter of interest, then $B_{low}$ may be shifted down but $B_{high}$ may remain unchanged. Thus, in the heart rate range for which there is no data, the effective range of parameter values considered to be normal ($B_{high}-B_{low}$) is increased, thereby decreasing false positive alarms.

In an alternate embodiment, user information may alter the baselining update process. For example, if a person is in an unusual situation (e.g. very sick), it may be desirable to suspend band updating for that period. The unusual condition could be communicated to the device via the programmer 68 (FIG. 1) or by other suitable means.

As described with reference to FIGS. 5 and 6, data associated with rapid heart rate changes is preferably excluded from the computation of $B_{low}$ and $B_{high}$. It may be desirable to exclude other data as well. For example, if a person tends to experience vasospasm, which may occur during a particular part of the day (e.g. Prinzmetal's angina tends to flare up while a person is asleep), that doesn't rise to the level of a cardiac event detection, then $B_{low}$ and $B_{high}$ should not reflect this transitory event. (The changes may not trigger a cardiac event detection for a number of reasons; primarily because the changes may not be sufficiently persistent to warrant detection (see block 732 of FIG. 7b).)

Figure 10:
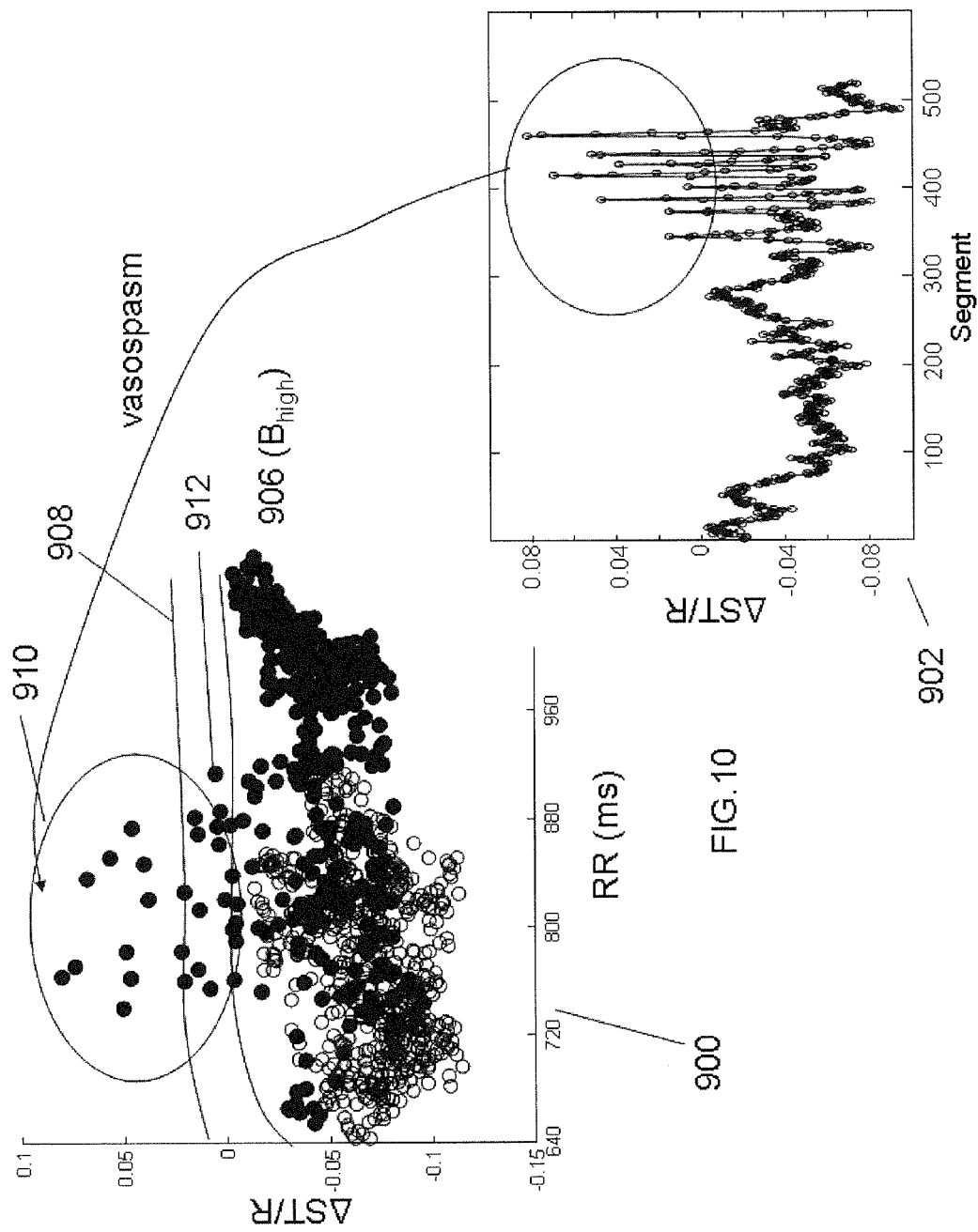
FIG. 10 shows ST/RR and ST trajectory plots for a patient that experienced vasospasm.

FIG. 10 shows data from a patient with Prinzmetal's angina (European Long Term ST database, www.physionet.org, record #2). Plot 900 is a scatter plot of ST deviation vs. RR interval for two sets of data. The data set with the empty circles corresponds to recordings made during the late morning/early afternoon; the data set with the filled circles corresponds to recordings taken during the following morning (from about 4 am to 8 am). An upper bound $B_{high}$ 906 is shown, along with a corresponding upper threshold 908 (corresponding to TH,h in block 727 of FIG. 7b). Plot 902 shows ST segment deviation for the latter data set, with the x axis representing segment number (each 10 second segment selected every 30 seconds).

Starting at approximately segment number 350 (just before 7 am), the patient experienced a run of significant ST elevation events, very likely caused by Prinzmetal's angina, which the patient was diagnosed with. These events caused the ST deviation to exceed the threshold 908 only for a few segments and thus preferably did not meet the persistence criteria. (I.e. block 732 in FIG. 7b would always pass control to block 729.) However, according to the present invention, the circled data 910 in plot 900 is excluded from the determination of upper band $B_{high}$ 906. Yet the data 910 is preferably tagged and recorded (as separate events, one for each peak in the circle in plot 902), and may alone or in combination with other data result in the detection of an event (e.g. unusually numerous vasospasms at an unusual time or vasospasms coupled with a persistent slow change in ST deviation).

Block 729 of FIG. 7b handles parameter changes that were not large enough to detect a certain type of cardiac event, but were large enough to indicate that the data should be excluded from bands and possibly should be associated with the detection of a different type of cardiac event. The number of different occasions that a parameter exceeded its block 728 threshold is counted over a rolling n hour period, where n is preferably set to the same period that bands are recomputed. If the count of such occurrences exceeds a programmable threshold, a non-emergency event may be detected.

The data associated with these occurrences may be appropriately tagged and stored. In any event, it is not used to compute bands. Even if certain RR/parameter value data points are not less than the block 728 threshold, if these data points are part of an event that was excluded from the band calculation, then these points are also preferably excluded. These points may be identified by, for example, searching for points close in time to the points that exceed either the block 727 or block 728 thresholds. For example, with reference to FIG. 10, point 912 is not less than the block 728 threshold but is nonetheless excluded from band calculations because it is part of the subsequent ST elevation event.

Regarding the storage of data that will be used to compute bands, each segment's RR(i) and $P_{avg}(i)$ may be stored in histogram format as described in U.S. patent application Ser. No. 10/950,401, filed October 2004, entitled "Implantable System for Monitoring the Condition of the Heart" to Fischell et al. $B_{low}$ and $B_{high}$ may be constructed from these histograms. Alternatively, the current and $P_{avg}(i)$ could be compared with the maximum and minimum stored values of the parameter near the heart rate range associated with RR(i). If the current $P_{avg}(i)$ is greater than the maximum, it is stored as the new maximum and an analogous procedure is followed if $P_{avg}(i)$ is less than the maximum. Otherwise, the current $P_{avg}(i)$ could be discarded.

Although $B_{low}$ and $B_{high}$ have been described as quadratic polynomials, they could be constructed by piecewise lines.

An alternate embodiment will be described with reference to FIG. 9. The average band curve 804a may be used as a band and the curves 800a and 802a, shifted by a desired amount, may be regarded as the heart rate related thresholds to apply.

Parameters

FIG. 11 shows some of the parameters that may be processed according to the teachings of the present invention. QRS slopes are preferably normalized by peak-to-peak QRS amplitude; normalizing in this fashion may reduce slope variability associated with axis shifts since larger slopes are often associated with larger peak-to-peak amplitudes. The minimum of the ST segment ($ST_{min}$) in the example shown occurs at the QRS offset point. However, in many instances, especially in the case of chronic ischemia or the like, $ST_{min}$ may occur between the QRS offset point and the rise of the T wave. The duration between the QRS offset point and $ST_{min}$ and/or the duration between the QRS offset point and the time the ST segment reaches 0 (defined as the voltage at which the QRS onset point occurs) are also possibly important parameters.

Pathologies

FIGS. 12a and 12b are a table that shows various pathologies and associated electrocardiographic changes, including the likely time course of such changes. A disease may affect electrocardiographic recordings by many different direct and indirect mechanisms. For example, congestive heart failure may slow cardiac wave propagation, and therefore alter the properties of the QRS complex, through a variety of mechanisms, including ion channel alterations, conductivity of heart tissue, and anatomical remodeling of the heart. Heart failure may also decrease QRS amplitudes, recorded subcutaneously or from the body surface, when it leads to generalized edema, which changes the effective resistance between the heard and subcutaneous/body surface electrode.

With regard to ST/T/U changes, most of the listed pathologies in the table will cause repolarization abnormalities throughout large portions of the heart. For example, pericarditis likely induces ischemic like reactions in large portions of the epicardium. This results in an epicardial to endocardial repolarization gradient, which the authors believe will manifest itself as ST segment elevation as seen by a lead, such as lead 12 (FIG. 1), that is aligned with the long axis of the heart, with a positive to negative polarity from lower left (e.g. electrode 13) to upper right (e.g. electrode 14). This is consistent with the common clinical finding of diffuse ST segment elevation, including ST elevation in limb lead II, in the case of pericarditis. Similarly, a can-to-tip polarity for a tip electrode within the inner surface of the heart should record ST depression in such cases.

More generally, any pathology associated with diffuse (12 lead) ST/T/U changes that tend to be significant in limb lead II (or lead aVR) should cause similar ST changes in the lead 12 and an intracardiac lead within the tip inside the heart. Lead II changes will have the same polarity as lead 12 changes and opposite polarity in a can-to-tip intracardiac lead. (Lead aVR changes are opposite lead II changes.) With regard to chronic ischemia, the possible mechanisms underlying the global nature of ST segment changes are discussed in Hopenfeld B., "ST segment depression: the possible role of global repolarization dynamics", Biomed Eng Online. 2007 Feb. 9; 6:6.

The pathologies that cause longer term changes may be tracked in different manners. As mentioned, the periodically performed band ($B_{high}$ and $B_{low}$) computation process can determine whether the bands are changing over a number of hours. Longer term trends, e.g. caused by chronic ischemia, may also be tracked as previously mentioned in the section entitled "obtaining bands". Another possibility for tracking changes on the order of hours would be to appropriately modify the choice of α's in block 722 of FIG. 7a. An alternative to this scheme involves computing the low pass filtered parameter slopes $\Delta P_{high}$ and $\Delta P_{low}$ only for relatively low heart rates to remove complications associated with rate related changes. (As previously mentioned, examination of rate related changes may serve as a different basis for detecting a cardiac event.)

What is claimed is:

1. A cardiac event detection system for detecting a cardiac event in a patient, comprising:
 (a) at least two sensors for sensing an analog signal from said patient's heart;
 (b) a device coupled to said sensors, said device having an analog-to-digital circuit system contained therein for digitizing said electrical signal to produce a digitized waveform of a heart rate of said patient over as plurality of heart beats, said heart rate defining a first parameter;
 (c) a processor electrically coupled to said analog-to-digital circuit system, said processor configured for:
  (i) computing both a heart rate time series data and a second parameter value data from the digitized waveform over said plurality of heart beats;
  (ii) low pass filtering and averaging of the heart rate time series data and the second parameter value data over a plurality of heart beats, thereby producing filtered and averaged heart rate time series data and filtered parameter value data;
  (iii) establishing upper and lower boundary values of the filtered and averaged heart rate time series;
  (iv) comparing the filtered parameter value data of at least one heart beat with said upper and lower boundary values;

(v) performing a cardiac event detection test based upon comparing the filtered parameter value data of at least one beat with said upper and lower boundary values that are determined from upper and lower normal boundaries established from the filtered and averaged heart rate time series data.

2. The system of claim 1, wherein the processor is further configured to compute the upper and lower normal boundaries.

3. A cardiac event detection system for detecting a cardiac event in a patient, comprising:
(a) at least two sensors for sensing an analog signal from said patient's heart;
(b) a device coupled to said sensors, said device having an analog-to-digital circuit system contained therein for digitizing said electrical signal to produce a digitized waveform;
(c) a processor electrically coupled to said analog-to-digital circuit system, said processor configured to:
  (i) compute from the digitized waveform both heart rate data and parameter value data;
  (ii) exclude a first parameter value data set as a function of heart rate from said parameter value data, said first parameter value data set associated with normal sinus rhythm and excluded from a determination of upper and lower boundary values of the value of the parameter as a function of heart rate;
  (iii) generate upper and lower normal boundary values based upon a second set of parameter value data defining a non-excluded parameter set as a function of heart rate;
  (iv) perform a cardiac event detection test that involves comparing a value of the parameter with its associated heart rate dependent upon said upper and lower normal boundary values.

4. The system of claim 3, wherein the parameter value data selected for exclusion is associated with as rapid change in heart rate.

5. The system of claim 3, wherein the parameter value data selected for exclusion is associated with a cardiac event that does not persist for longer than a predetermined threshold.

6. A cardiac event detection system for detecting a cardiac event in a patient, comprising:
(a) at least two sensors for sensing an analog signal from said patient's heart;
(b) a device coupled to said sensors, said device having an analog-to-digital circuit system contained therein for digitizing said electrical signal to produce a digitized waveform;
(c) a processor electrically coupled to said analog-to-digital circuit system, said processor configured to:
  (i) compute from the digitized waveform heart rate data;
  (ii) low pass filter the heart rate data, thereby producing filtered heart rate data;
  (iii) compute a change in the heart rate from the filtered heart rate data;
  (iv) perform a cardiac event detection test, as a function of the computed change in heart rate.

7. The system of claim 6, wherein the processor is configured to perform a cardiac event detection test only if the change in heart rate is less than a predetermined threshold.

8. A cardiac event detection system for detecting as cardiac event in a patient, comprising:
(a) at least two sensors for sensing an analog signal from said patient's heart;
(b) a device coupled to said sensors, said device having an analog-to-digital circuit system contained therein for digitizing said electrical signal to produce a digitized waveform;
(c) a processor electrically coupled to said analog-to-digital circuit system, said processor configured to:
  (i) compute from the digitized waveform both heart rate data and parameter value data;
  (ii) compute the value of as function of changes in the value of the parameter;
  (iii) correcting the value of the function according to a change in heart rate, thereby generating a corrected function value
  (iv) perform a cardiac event detection test based on the corrected function value.

9. The system of claim 8, wherein the function is an estimate of the average value of the change in parameter over time.

* * * * *